(12) United States Patent
Lacko et al.

(10) Patent No.: US 9,314,532 B2
(45) Date of Patent: *Apr. 19, 2016

(54) DRUG DELIVERY VEHICLE

(71) Applicants: University of North Texas Health Science Center, Fort Worth, TX (US); The United States of America, as represented by the Secretary, Department of Health and Human Services, Bethesda, MD (US)

(72) Inventors: Andras G. Lacko, Fort Worth, TX (US); Alan T. Remaley, Bethesda, MD (US); Nirupama A. Sabnis, Fort Worth, TX (US)

(73) Assignees: University of North Texas Health Science Center, Fort Worth, TX (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/961,296

(22) Filed: Aug. 7, 2013

(65) Prior Publication Data

US 2014/0045950 A1 Feb. 13, 2014

Related U.S. Application Data

(60) Provisional application No. 61/682,057, filed on Aug. 10, 2012.

(51) Int. Cl.

| | |
|---|---|
| A61K 47/48 | (2006.01) |
| A61K 31/337 | (2006.01) |
| A61K 31/351 | (2006.01) |
| A61K 31/415 | (2006.01) |
| A61K 9/107 | (2006.01) |
| A61P 35/00 | (2006.01) |
| C07K 14/47 | (2006.01) |
| C07K 7/06 | (2006.01) |
| C07K 7/08 | (2006.01) |
| A61K 47/42 | (2006.01) |
| A61K 31/7105 | (2006.01) |

(52) U.S. Cl.
CPC .............. *A61K 47/42* (2013.01); *A61K 31/337* (2013.01); *A61K 31/415* (2013.01); *A61K 31/7105* (2013.01); *A61K 47/488* (2013.01); *A61K 47/48038* (2013.01); *A61K 47/48315* (2013.01)

(58) Field of Classification Search
None
See application file for complete search history.

(56) References Cited

U.S. PATENT DOCUMENTS

| 7,572,771 | B1 | 8/2009 | Remaley et al. |
|---|---|---|---|
| 7,951,402 | B2 | 5/2011 | Lanphere et al. |
| 8,071,746 | B2 | 12/2011 | Remaley et al. |
| 8,206,747 | B2 | 6/2012 | Zale et al. |
| 8,246,968 | B2 | 8/2012 | Zale et al. |
| 2008/0145439 | A1 | 6/2008 | Lobl et al. |
| 2009/0001107 | A1 | 1/2009 | Ambs |
| 2009/0081293 | A1 | 3/2009 | Murase et al. |
| 2009/0170960 | A1 | 7/2009 | Kusumoto et al. |
| 2010/0068286 | A1 | 3/2010 | Troiano et al. |
| 2010/0069426 | A1 | 3/2010 | Zale et al. |
| 2010/0087337 | A1 | 4/2010 | DeWitt |
| 2010/0104645 | A1 | 4/2010 | Ali et al. |
| 2010/0104655 | A1 | 4/2010 | Zale et al. |
| 2010/0216804 | A1 | 8/2010 | Zale et al. |
| 2010/0226986 | A1 | 9/2010 | Grayson et al. |
| 2010/0266642 | A1 | 10/2010 | Langer et al. |
| 2011/0002173 | A1 | 1/2011 | Nagamatsu et al. |
| 2011/0003128 | A1 | 1/2011 | Isozaki et al. |
| 2011/0275704 | A1 | 11/2011 | Troiano et al. |
| 2014/0045950 | A1 | 2/2014 | Lacko et al. |

FOREIGN PATENT DOCUMENTS

| WO | 2007/145659 A1 | 12/2007 |
|---|---|---|
| WO | 2008/094905 A2 | 8/2008 |
| WO | 2009/073984 | 6/2009 |
| WO | WO 2010057203 A2 * | 5/2010 |
| WO | WO 2011066511 A1 * | 6/2011 |

OTHER PUBLICATIONS

Shen et al., "Synthesis and characterization of RGD-fatty acid amphiphilic micelles as targeted delivery carriers for anticancer agents," J. Drug Targeting 15:51-58 (2007).*

European Patent Office; International Search Report and Written Opinion; PCT Application No. PCT/US2013/053953; Oct. 16, 2013.

Javali, Narashima M., et al; Fatty Acid-RDG Peptide Amphiphile Micelles as Potential Paclitaxel Delivery Carriers to Alpha(v) Beta(3) Integrin Overexpressing Tumors; Pharmaceutical Research, vol. 29, No. 12, Dec. 2012, pp. 3347-3361.

Massaguer, A., et al; Synthesis of RGD Containing Peptides. Comparative Study of Their Incorporation to the Surface of 5-Fluoridine Loaded Liposomes; Journal of Liposome Research, vol. 11, No. 1, Apr. 1, 2001; pp. 103-113.

Ramprasad, M.P., et al; Sustained-Delivery of an Apolipoproteine-Peptidomimetic Using Multivesicular Liposomes Lowers Serum Cholesteral Levels; Journal of Controlled Release, vol. 79, No. 1-3, Feb. 19, 2002, pp. 207-218.

Navab, M., et al; Apolipoprotein A-I Mimetic Peptides; Arteriosclerosis, Thrombosis, and Vascular Biology, vol. 25, No. 7, Apr. 14, 2005; pp. 1325-1331.

Thuahnai, S.T., et al; A Quantitative Analysis of Apolipoprotein Binding to SR-BI: Multiple Binding Sites for Lipid-Free and Lipid-Associated Apolipoproteins; vol. 44, No. 6, Jun. 2003, pp. 1132-1142.

(Continued)

*Primary Examiner* — Julie Ha
*Assistant Examiner* — Kristina M Hellman
(74) *Attorney, Agent, or Firm* — Jackson Walker LLP

(57) ABSTRACT

The present disclosure provides targeted drug delivery vehicle compositions comprising a drug composition and targeted poly-amino-acid subunits, methods of manufacture, and methods of treatment for numerous diseases.

31 Claims, 10 Drawing Sheets

(56) References Cited

OTHER PUBLICATIONS

Shin, Jae-Yoon et al.; PH-Responsive High-Density Lipoprotein-Like Nanoparticles to Release Paclitaxel at Acidic PH in Cancer Chemotherapy; International Journal of Nanomedicine, vol. 7, 2012, pp. 2805-2816.

Tabet, Fatiha, et al; The 5A Apolipoprotein A-I Mimetic Peptide Displays Antiinflammatory and Antioxidant Properties In Vivo and In Vitro; Arteriosclerosis Thrombosis and Vascular Biology, vol. 30, No. 2, Feb. 2010, pp. 246-252 + 5 pages of supplemental material.

Lacko, Andras G., et al; Prospects and Challenges of the Development of Lipoprotein-Based Formulations for Anti-Cancer Drugs; Expert Opinion on Drug Delivery, vol. 4, No. 6, Nov. 2007, pp. 665-675.

Choi, et al; Protease-Activated Drug Development; Theranostics 2012:2(2):156-78, Epub Feb. 2012.

Peer, et al; Nanocarriers as an Emerging Platform for Cancer Therapy; Nat. Nanotechnol. Dec. 2007, 2(12):751-60.

Ng, et al; Lipoprotein-Inspired Nanoparticles for Cancer Theranostics; Acc Chem Res. Oct. 18, 2011; 44(10):1105-13, Epub May 10, 2011.

Sabnis, et al; Enhanced Solubility and Functionality of Valrubicin (AD-32) Against Cancer Cells Upon Encapsulation Into Biocompatible Nanoparticles; Int J Nanomedicine; 2012, 7:975-83, Epub Feb. 22, 2012.

Shahzad, et al; Targeted Delivery of Small Interfering RNA Using Reconstituted High-Density Lipoprotein Nanoparticles; Neoplasia, Apr. 2011, 13(4):309-19.

Eisenberg, et al; Hydrophobic Moments and Protein Structure; Faraday Symp. Chem. Soc. 1982; 17:109-120.

Eisenberg, et al; The Hydrophobic Moment Detects Periodicity in Protein Hydrophobicity; Proc. Natl. Acad. Sci USA, Jan. 1894, 81(1):140-4.

Eisenberg, et al; Analysis of Membrane and Surface Protein Sequences With the Hydrophobic Moment Plot; J. Mol. Biol. Oct. 15, 1984: 179(1):125-42.

\* cited by examiner

Figure 5

| Cell Lines Used | IC$_{50}$ For Free-AD32 (µM) | IC$_{50}$ For Myr5A-AD32 (µM) |
|---|---|---|
| Non Malignant | | |
| PZ-HPV | 9.5 | 15 |
| HiO180 | 19.8 | 36 |
| Malignant | | |
| PC-3 | 19.3 | n/a |
| SKOV-3 | 21.5 | 13 |

Figure 6 A and B

Figure 8

| Sample | Peptide ID # | ³H-paclitaxel CPM | |
|---|---|---|---|
| | | Initial (total count/%) | After Dialysis (total count/%) |
| 1 | 37874 | 29868/100 | 27371/91.63 |
| 2 | 37875 | 30526/100 | 26544/86.96 |
| 3 | 37877 | 23222/100 | 22957/98.86 |
| 4 | 37878 | 37032/100 | 36810/99.38 |
| 5* | 30722 | 23830/100 | 22820/95.76 |

DRUG DELIVERY VEHICLE

This application claims the benefit of U.S. Provisional Patent Application Ser. No. 61/682,057, entitled DRUG DELIVERY VEHICLE, filed on Aug. 10, 2012, the entire content of which is hereby incorporated by reference.

STATEMENT REGARDING FEDERALLY SPONSORED RESEARCH

This invention was made with the support, in parts, of the Intramural Heart, Lung, and Blood Institute Research Fund. The government has certain rights in the invention.

BACKGROUND

This application pertains to compositions for tailored drug delivery of a pharmaceutical agent to a specific cell, tissue, or organ type using naturally occurring affinities.

Many drug candidates fail to advance through the drug-development pipeline because of harmful side-effects. Often these problems are associated with the use of passive drug delivery, which relies on the absorption of a drug across the biological membrane of all cells. When systemically administered by passive drug delivery to a patient, many drugs will only reach the targeted cells in low concentrations, with the remaining drug either non-specifically collecting in other parts of the body (e.g. high concentrations in the liver and plasma) or being cleared from the body. This is of particular concern for drugs having a high cytotoxic potential, such as chemotherapy agents, which can damage healthy as well as diseased cells. A targeted delivery of pharmaceutical agents is highly desirable because via this mechanism accurate dosages of an effective drug may be delivered selectively to diseased cells and would either totally avoid or reduce the amount of drug exposure to normal, healthy cells and tissues.

Different types of drug delivery vehicles have been explored such as, polymeric micelles, polymeric nanovehicle, liposomes, polymersomes, nanospheres, nanocapsules, dendrimers, proteins, cell ghosts, inorganic/metallic and bacterial delivery vehicles (Alexis et al. 2010; Matsumura and Kataoka 2009; Wang et al. 2009). Many of these approaches require the use of large proteins which may be expensive to produce. Additionally, many of the currently employed drug delivery vehicles fail to address the problem of simultaneously impacting healthy cells and tissues via the drug employed.

Ideally, a targeted drug delivery vehicle should act specifically on the diseased cell of interest, while avoiding toxic side-effects on healthy cells. Furthermore, the delivery agent should be largely non-immunogenic, have extended residence time in the blood and be biodegradable. Furthermore, the system as whole should be amenable to address a broad range of diseases and be amenable to scale up and manufacturing at a commercial-scale level.

The current invention provides drug delivery compositions, methods of manufacture and methods of treatment for therapeutic applications that can overcome several challenges currently presented in pharmaceutical development.

SUMMARY OF THE INVENTION

This application pertains to compositions for tailored drug delivery of a pharmaceutical agent to a specific cell, tissue, or organ type using naturally occurring affinities.

In some embodiments the invention provides a composition comprising a targeting amino acid chain bound to a biocompatible polymer. In some embodiments, the composition can increase the solubility of a drug. In some embodiments the biocompatible polymer is a fatty acid. In some embodiments the fatty acid is a saturated fatty acid. In some embodiments the fatty acid is a fatty acid chain smaller than 15 carbons in length. In some embodiments biocompatible polymer is myristic acid. In some embodiments the targeting amino acid chain is covalently linked to the biocompatible polymer.

In some embodiments the targeting amino acid chain is smaller than 50 amino acids in length. In some embodiments the targeting amino acid chain has an affinity to a transmembrane molecule. In some embodiments the targeting amino acid chain has an affinity to a receptor. In some embodiments the targeting amino acid chain has an affinity to an HDL receptor. In some embodiments the targeting amino acid chain has an affinity to rapidly dividing cells. In some embodiments the targeting amino acid chain has an affinity to cancer cells. In some embodiments the targeting amino acid chain is selected from a group consisting of SEQ ID NO: 1-62.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Some novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 shows comparative cytotoxicity studies of drug-loaded vehicle compared to conventional passive drug delivery on cancerous cell lines (PC-3 prostate and SKOV-3 ovarian cancer cell lines) and non-malignant cell lines (PZ-HPV and HiO180). The in vitro therapeutic index is thus increased by at least 80 fold when the drug valrubicin is incorporated into rHDL nanoparticles.

FIG. 8 shows paclitaxel encapsulation efficiency into myristoyl peptide nanoparticles based on measurements of 3H-paclitaxel.

DEFINITIONS

Figure 1:
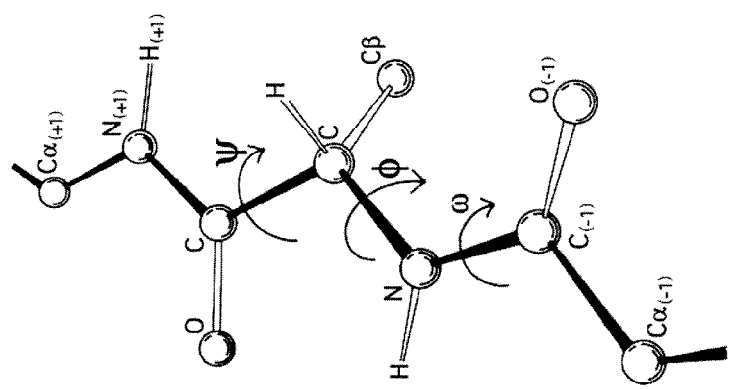
FIG. 1 shows a Ramachandran plot ([$\phi,\psi$]) plot that illustrates the definition of the $\phi$ and $\psi$ backbone dihedral angles that are used to define an alpha helix confirmation.

The term "treat", "treating" or "treatment" refers to any indication of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

The term "administering" refers to oral administration, administration as a suppository, topical contact, parenteral, intravenous, intraperitoneal, intramuscular, intralesional, intranasal or subcutaneous administration, intrathecal administration, intra-lymphatic, inhalation of microdroplets, or the implantation of a slow-release device e.g., a mini-osmotic pump, to the subject.

The term "therapeutically-effective amount or dose" or "therapeutically sufficient amount or dose" or "effective or sufficient amount or dose" refer to a dose that produces therapeutic effects for which it is administered. In sensitized cells, the therapeutically effective dose can often be lower than the conventional therapeutically effective dose for non-sensitized cells.

The term "agent" or "biologically active agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the alike. A skilled artisan can readily recognize that there is no limit as to the structural nature of the agents of the present invention.

The term "prodrug" means any form of a drug (or compound) which is administered to an patient, such as a human, in an inactive or less active than the original structure. Prodrugs can be converted, to the active form by metabolization. Said conversion of the prodrug into the active form is not specifically restricted to any chemical and/or physical alteration of the prodrug which occurs after administration, such as release of an active part (particularly the cytostatic agent) of the prodrug at the site of action.

The term "affinity binding" refers to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions.

The term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic molecules have a hydrophilic head group and a hydrophobic tail group, where the hydrophobic group and hydrophilic group are joined by a covalent bond, or by a variable length linker group.

The term "subject," "individual" or "patient" is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

The term "in vivo" refers to an event that takes place in a subject's or animal's body.

The term "in vitro" refers to an event that takes places outside of a subject's or animal's body. For example, an in vitro assay encompasses any assay run outside of a subject assay. In vitro assays encompass cell-based assays in which cells, alive or dead, are employed. In vitro assays also encompass a cell-free assay in which no intact cells are employed.

The term "targeting molecule", refers to all molecules capable of specifically binding to a particular target and forming a bound complex. For example, the ligand and its corresponding target molecule, an antibody, form a specific binding pair that forms a complex when bound together by their corresponding affinity bonding sites.

The term "$C_{max}$" refers to the peak plasma concentration of the drug after administration.

The term "$T_{max}$" refers to the length of time to takes to reach the peak plasma concentration of the drug after administration.

The term "AUC" refers to the area under a curve and indicates the integral of the concentration-time curve after a single dosage or in a steady state after administration of the drug.

DETAILED DESCRIPTION

Herein, we provide compositions for tailored drug delivery of pharmaceutical agents to a specific cell, tissue or organ type using, naturally occurring affinities, an efficient method for commercial scale manufacture and methods for treatment across a broad range of therapeutics and diseases.

Targeting Amino Acid Chain

The present invention provides targeted drug delivery vehicles comprising a poly amino acid composition comprised of a targeting amino acid chain. The targeting amino acid chain generally has an affinity for a target or target related molecule which will help the targeted drug delivery vehicle find, bind to, or otherwise interact with a target. This targeting can be useful for delivering a drug to a target.

The targeting amino acid chain can have homology to a naturally occurring full-length protein. For example, the targeting amino acid chain can be a peptide that is a portion of a larger naturally occurring protein. In some embodiments the targeting amino acid chain is a peptide that is identical to a portion of a naturally occurring protein. In other embodiments modification from the natural sequence are made to a portion of the peptide, altering the sequence from that found naturally, for example by 1%, 5%, 10%, 20%, or 30%. In some embodiments non-naturally occurring molecules are included in the amino acid chain.

The targeting amino acid chain may be comprised of less than 50 amino acids. Alternatively, the targeting amino acid chain can be comprised of about 50 to 40 amino acids, about 40 to 30 amino acids, about 30 to 20 amino acids, about 20 to 10 amino acids, or about 10 to 5 amino acids in length. In some instances the targeting amino acid chain is larger than 50 amino acids or is comprised of multiple repeating targeting amino acid chains. In some embodiments the repeating targeting amino acid chains have similar or identical compositions.

The targeting amino acid chains, or any acids of the invention can in certain applications be comprised of natural or unnatural amino acid residues. Additionally, the targeting amino acid chain can be derived from a combination of natural or not naturally occurring amino acid residues. For example, the targeting amino acid chain can have a backbone that is partially or completely non-amino acid in nature, but contain side groups identical to the side groups of the amino acid residues that occur in the amino acid chain on which the targeting amino acid chain is modeled. Several types of chemical bonds, for example, ester, thioester, thioamide, retroamide, reduced carbonyl, dimethylene and ketomethylene bonds, are generally useful substitutes for amino acid chain bonds in the construction of protease-resistant targeting molecules.

The targeting amino acid chain can comprise one or more alpha helix ($\alpha$-helix) or $\alpha$-helixes, for example the targeting amino acid chain can comprise two $\alpha$-helixes. The $\alpha$-helix is a confirmation that is characterized by a right-handed coiled or spiral conformation, in which every backbone N—H group donates a hydrogen bond to the backbone C=O group of the amino acid four residues prior. Helices observed in proteins can range from four to over forty amino acid residues long.

Amino acid residues comprising an $\alpha$-helix typically adopt backbone ($\phi$, $\psi$) dihedral angles around ($-60°$, $-45°$). The alpha-helices structures can be identified in using several computational methods, one of which is the Dictionary of Protein Secondary Structure. $\alpha$-helices adopt dihedral angles such that the $\psi$ dihedral angle of one residue and the $\phi$ dihedral angle of the next residue sum to roughly $-105°$. As a consequence, $\alpha$-helical dihedral angles, in general, fall on a diagonal stripe on the Ramachandran plot or ($[\phi,\psi]$ plot), diagram (of slope $-1$), ranging from ($-90°$, $-15°$) to ($-35°$, $-70°$). For comparison, the sum of the dihedral angles for a 310 helix is roughly $-75°$, whereas that for the $\pi$-helix is roughly $-130°$. The general formula for the rotation angle $\Omega$ (omega) per residue of any amino acid chain helix with trans isomers is determined by the following equation:

$$3 \cos \text{Omega} = 1 - 4 \cos^2[(\text{phi} + \text{psi})/2].$$

There is a multiplicity of techniques available for constructing targeting amino acid chain with the same, similar or increased biological affinity as the corresponding native peptide. Amino acids chain can be constructed to exhibit one or more desired activities that are distinct or improved from the corresponding native peptide. By way of example, an amino acid chain can be developed to have improved characteristics of solubility, stability, lipid interaction, and/or susceptibility to hydrolysis or proteolysis (Morgan and Gainor, Ann. Rep. Med. Chem. 24:243-252, 1989) or other characteristics that enhance their therapeutic application, such as increased cell permeability, greater affinity and/or avidity for a binding partner, and/or prolonged half-life inside the cell.

Amino acids are largely classified according to their side chains into the following categories: polar, hydrophobic, acidic, basic and aromatic. Polar amino acids include, without limitation, asparagines, cytokine, glutamine, histamine, selenocysteine, serine, threonine, tryptophan and tyrosine. Examples of hydrophobic or non-polar amino acids include, without limitation, leucine, isoleucine, valine, glycine, alanine, proline, methionine, and phenylalanine. Examples of basic amino acid residues include, without limitation, arginine, homolysine and lysine. Examples of acidic amino acid residues include, without limitation, aspartic acid and glutamic acid. Aromatic amino acids include, without limitation, biphenylalanine, histidine, 2-napthylalananine, pentafluorophenylalanine, phenylalanine, tryptophan and tyrosine. Some amino acids are classified in more than one group, for example, histidine, tryptophan and tyrosine are classified as both polar and aromatic amino acids. Additional amino acids in these categories are known.

Different amino-acid sequences have different propensities for forming $\alpha$-helical structure. The amino acids, methionine, alanine, leucine, uncharged glutamate, and lysine have especially high helix-forming propensities, whereas proline and glycine have poor helix-forming propensities. The amino acid, proline can break a helix structure for the reason that its sidechain interferes sterically with the backbone of the preceding turn, forcing a bend in the helix axis. However, proline is often seen as the first residue of a helix, presumably owing to its structural rigidity. At the other extreme, glycine, which has virtually no side chain, also tends to disrupt helices because its high conformational flexibility makes it entropically expensive to adopt the relatively constrained $\alpha$-helical structure.

By way of example, an amino acid chain's helical conformation can be affected by both the charge and hydrophobicity of the molecule at the target site and the bulk (or size) of the side chain which has been substituted in. Amino acid substitutions which are expected to produce the greatest changes in the amino acid chain's physical properties and confirmation can be, for example, if a hydrophilic residue, such as, seryl or threonyl, is substituted for a hydrophobic residue, such as, leucyl, isoleucyl, phenylalanyl, valyl or alanyl. An additional example is when an amino acid having a bulky side chain, such as, phenylalanine, is substituted for an amino acid lacking a side chain, such as, glycine.

Suitable substitutions for a targeting amino acid chain include, but are not limited to, beta-alanine and other omega-amino acids, such as 3-aminopropionic acid, 2,3-diaminopropionic acid, 4-aminobutyric acid and the alike, alpha-aminoisobutyric acid, epsilon-aminohexanoic acid, delta-aminovaleric acid, N-methylglycine or sarcosine, ornithine, citrulline, t-butylalanine, t-butylglycine, N-methylisoleucine, phenylglycine, cyclohexylalanine, norleucine, naphthylalanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, beta-2-thienylalanine, methionine sulfoxide, homoarginine, N-acetyl lysine, 2,4-diaminobutyric acid, 2,3-diaminobutyric acid, p-aminophenylalanine, N-methyl valine, homocysteine, homophenylalanine, homoserine, hydroxyproline, homoproline, N-methylated amino acids, and peptoids (N-substituted glycines).

The targeting amino acid chain can have amipathic properties. A targeting amino acid chain can have a hydrophilic property on one side of the alpha helix (α-helix) and has a hydrophobic property on the opposite side of the α-helix.

The degree of amphipathicity of the α-helixes can be quantified by calculating the hydrophobic moment ($\mu_H$) of each of the amphipathic α-helical domains. Methods for calculating $\mu_H$ are described in Eisenberg et al., Faraday Symp. Chem. Soc. 17:109-120, 1982; Eisenberg et al., PNAS 81:140-144, 1984; and Eisenberg et al., J. Mol. Biol. 179:125-142, 1984. The amphipathicities of various amino acid chains of different lengths can be directly compared by way of the mean hydrophobic moment. The mean hydrophobic moment per residue can be obtained by dividing $\mu_H$ by the number of residues in the amino acid chain.

The targeting amino acid chain allows for the tailored manufacture of the sequence for targeting to specific targets, e.g. specific cells tissues or organs associated with a disease. Generally this is achieved using protein chemistry methods to adapt or design the targeting amino acid chain such that it has an affinity to a target.

A targeting amino acid chain can advance towards and bind to a specific cell, tissue or organs types in the body by homing to its target that is has affinity to. The targeting amino acid chain can be designed, for example, by using tissue specific cell-surface molecules as model templates to engineer a synthetic targeting amino acid chain. Examples of suitable molecules that can be used as models for the targeting amino acid chain molecule include, but are not limited to, antibodies, antibody fragments, peptides, lymphokines, cytokines, receptor proteins, hormones, growth factors, ligands, sugars, carbohydrates, transmemebrane proteins or equivalents thereof.

The targeting amino acid chain can have an affinity to membrane-bound receptors that are tissue, cell or organ specific.

Suitable amino acid sequences that can be used to as the targeting molecule include, but are not limited, to heparin binding site (RKNR) (SEQ ID NO:1) or (KKWVR) (SEQ ID NO:2), integrin binding site (RGD) (SEQ ID NO:3), P-selectin (DVEWVDVSY) (SEQ ID NO:4), internalization sequence of TAT HIV (RKKRRQRRRPPQ) (SEQ ID NO:5) and (RRRQRRKKR) (SEQ ID NO:6), panning (RRPXR) (SEQ ID NO:7), penatratin (RQIKIWFQNRRMKWKK) (SEQ ID NO:8), neutral cholesterol esterase activation SAA C-terminus (GHEDTMADQEANRHGRSGGDPNYYRP-PGGY) (SEQ ID NO:9), inhibition of ACAT SAA N-terminus (GFFSFIGEAFQGAGDMWRAY) (SEQ ID NO:10), increase liver affinity LDL receptor (KAEYKKNKHRH) (SEQ ID NO:11) or (YTRLTRKRGLK) (SEQ ID NO:12), anti-oxidant activity modified 18A (DWLKAFYCKVAEK-LKEAF) (SEQ ID NO:13) or (DWLKAFYDKVAEKLK-CAF) (SEQ ID NO:14), apoA-I milano (YSDGLRQC-LAARLDALKDR) (SEQ ID NO:15), heavy metal chelation 6×-His sequence (HHHHHH) (SEQ ID NO:16), lactoferrin (FQWQRNIRKVR) (SEQ ID NO:17) and Scavenger receptor type B-1 (SR-B1) binding sequences, DWLKAFYDK-VAEKLKEAFPDWLKAFYDKVAEKLKEAF (SEQ ID NO:18), RMRITERDDFRGQMSEITDDCPSLQDRF-HLTEVHSLRVLEGS (SEQ ID NO:19), DWLKAFYDK-VAEKLKEAFPDWAKAAYDKAAEKAKEAA (SEQ ID NO:20), DWLKAFYDKVAEKLKEAFPDWLKAFYDK-VAEKAKEAF (SEQ ID NO:21), DWLKAFYDKVAEK-LKEAFPDWLKAFYDKVAEKAKEAA (SEQ ID NO:22), DWLKAFYDKVAEKLKEAFPDWLKAAYDK-VAEKAKEAA (SEQ ID NO:23), DWLKAFYDKVAEK-LKEAFPDWLKAAYDKAAEKAKEAA (SEQ ID NO:24), DWLKAFYDKVAEKLKEAFPDWGKAGYDK-GAEKGKEAG (SEQ ID NO:25), DWLKAFYDKVAEK-LKEAFPDWGKAGYDKGAEKGKEAF (SEQ ID NO:26), DWGKAGYDKGAEKGKEAGDWLKAFYDK-VAEKLKEAF (SEQ ID NO:27), DWLKAFYDKVAEK-LKEAFPDWLKAFYDKVAEKLK (SEQ ID NO:28), KAFYDKVAEKLKEAFPDWLKAFYDKVAEKLKEAF (SEQ ID NO:29), DWLKAFYDKVAEKLKEAFPD-WLKAFYDKVA (SEQ ID NO:30), DKVAEKLKEAFPD-WLKAFYDKVAEKLKEAF (SEQ ID NO:31), DWLKAFY-DKVAEKLKEAFPDWLKAFYKVAEKLKEAF (SEQ ID NO:32), DWLKAFYDKVAEKLKEAFPDWLKAFY-VAEKLKEAF (SEQ ID NO:33), DWLAFYDKVAEK-LKEAFPDWLKAFYDKVAEKLKEAF (SEQ ID NO:34), DWLFYDKVAEKLKEAFPDWLKAFYDKVAEKLKEAF (SEQ ID NO:35), DWLKAFYDKVAEKLKEAFPDW-LAKAFYDKVAEKLKEAF (SEQ ID NO:36), DWLKAFY-DKVAEKLKEAFPDWLAAKAFYDKVAEKLKEAF (SEQ ID NO:37), DWLKAAFYDKVAEKLKEAFPDWLKAFY-DKVAEKLKEAF (SEQ ID NO:38), DWLKAAAFYDK-VAEKLKEAFPDWLKAFYDKVAEKLKEAF (SEQ ID NO:39), DWLKAFYDKVAEKLKEAFPDWLEAFYDK-VAKKLKEAF (SEQ ID NO:40), DWLKAFYDKVAEK-LKEAFPDWLEAFYDEVAKKLKKAF (SEQ ID NO:41), DWLEAFYDKVAKKLKEAFPDWLKAFYDK-VAEKLKEAF (SEQ ID NO:42), DWLEAFYDE-VAKKLKKAFPDWLKAFYDKVAEKLKEAF (SEQ ID NO:43), DWLKAFYDKVAEKLKEAFPDWLKAFYDK-VAEKLKEAF (SEQ ID NO:44), DWLKAFYDKVAEK-LKEAFPDWLKAFYDKVAEKLKEAF (SEQ ID NO:45), DWLKAFYDKVAEKLKEAFPDWLKAFYDK-VAEKLKEAF (SEQ ID NO:46), DWLKAFYDKVAEK-LKEAFPDWLKAFYDKVAEKLKEAF (SEQ ID NO:47), LLDNWDSVTSTFSKLREQPDWAKAAYD-KAAEKAKEAA (SEQ ID NO:48), LESFKVSFLSA-LEEYTKKPDWAKAAYDKAAEKAKEAA (SEQ ID NO:49), DWAKAAYDKAAEKAKEAAPLLDNWDSVT-STFSKLREQ (SEQ ID NO:50), DWAKAAYD-KAAEKAKEAAPLESFKVSFLSALEEYTKK (SEQ ID NO:51), DWLKAFYDKVAEKLKEAFPSDELRQR-LAARLEALKEN (SEQ ID NO:52), DWLKAFYDKVAEK-LKEAFPRAELQEGARQKLHELQEK (SEQ ID NO:53), SDELRQRLAARLEALKENPDWLKAFYDK-VAEKLKEAF (SEQ ID NO:54), RAELQEGARQKL-HELQEKPDWLKAFYDKVAEKLKEAF (SEQ ID NO:55), LLDNWDSVTSTFSKLREQPSDELRQR-LAARLEALKEN (SEQ ID NO:56), LESFKVSFLSA-LEEYTKKPRAELQEGARQKLHELQEK (SEQ ID NO:57), SDELRQRLAARLEALKENPLLDNWDSVT-STFSKLREQ (SEQ ID NO:58), LLDNWDSVTSTFSKL-REQPLESFKVSFLSALEEYTKK (SEQ ID NO:59), DWLKAFYDKVAEKLKEAFPDWLRAFYDK-VAEKLKEAF (SEQ ID NO:60), DWLKAFYDKVAEK-LKEAFPDWLRAFYDRVAEKLKEAF (SEQ ID NO:61), DWLKAFYDKVAEKLKEAFPDWLRAFYDR-VAEKLREAF (SEQ ID NO:62).

The targeting amino acid chain can have an affinity to a molecule that specifically localizes to the desired surface of the target cell affected by the disease to be treated. In one embodiment, cell-type specific molecules are used as templates to build a synthetic targeting molecule comprising the poly amine-acid subunit. Tissue sites envisioned to be targeted by the targeting molecule include, but are not limited to, neural cells, liver cells, bone marrow cells, kidney cells, pancreatic cells, stem cells, progenitor cells, lymphocytic cells, muscle cells, gastric tissue, lung tissue, brain tissue and other disease cells such as cancerous, hyperproliferative, or undifferentiated cells.

In addition to using cell surface and cell-type specific molecules as models to construct a targeting amino acid chain, one can also perform an in vivo or in vitro assays to determine a particular targeting sequence for a disease of interest. Accordingly, in one embodiment the invention provides methods to make several degenerate peptides and then introduce the degenerate peptides into an animal model or cell culture system representative of the disease to be treated. The diseased cells will be extracted and protein analysis will be performed (such as protein sequencing by mass spectrometry and/or Edman degradation reaction to determine which degenerate peptides localized to the diseased cells). Once determined, the targeting sequence will used to build the targeting amino acid chain. In one embodiment of the invention, the experimentally determined amino acid sequence is the targeting molecule that comprises targeting amino acid chain. In another embodiment, targeting amino acid chain is comprising the experimentally determined targeting amino acid sequence is constructed into a drug delivery vehicle and used for treatment of the disease and its equivalent diseases using an appropriate pharmaceutical agent in a therapeutic-effective amount.

Examples of targeting molecules that can be used can include cell surface and tissue-specific molecules as discussed earlier. In addition, targeting conjugates can be used. In this application of the invention, one of the targeting conjugates would be placed at the disease site while its conjugate partner is present on the targeted drug vehicle; ultimately the targeting conjugate combination provide the drug vehicle the ability to advance towards the disease site. Examples of targeting conjugates include, but are not limited to, a combination of biotin and avidin, a combination of biotin and streptavidin, a combination of biotin and NeutrAvidin®, a combination of biotin and human-derived biotin-binding molecules, a combination of biotin and Strep-Tactin®, a combination of Strep-Tag® and Strep-Tactin®, a combination of Strep-TagII® and Strep-Tactin®, a combination of S-Tag® and S-protein, a combination of Halo Ligand® and Halotag®, a combination of glutathione and glutathione S-transferase, a combination of amylose and a maltose-binding protein, a combination of appropriately designed epitope and a humanized monoclonal antibody for the epitope, and a combination of appropriately designed sugar chains and relevant sugar chain-recognizing molecules including lectin and humanized monoclonal antibodies. Herein, biotin, glutathione, a sugar, an epitope, or the a like may be modified with a spacer arm (e.g., polyethylene glycol or hydrocarbon) and a reaction group (e.g., an N-hydroxysuccinimide group, a sulfo-N-hydroxysuccinimide group, a pentafluorophenyl group, a hydrazide group, an amide group, a pentylamine group, a maleimide group, a hexyl(pyridyldithio)propionamide group, a iodoacetyl group, a ridyl group, an azidosalicylamide group, a nitrophenyl azide group, a psoralen group, or a tetraphenylfluoroazido group).

Additionally, a combination of complementary nucleic acids thereof, a combination of an antigen and an antibody or a fragment thereof, a combination of an enzyme and a substrate or an inhibitor, or a combination of a ligand and a receptor can be also be used as a targeting conjugates with the claimed invention.

The invention also provides for a composition, wherein the poly amine-acid subunit is comprised of at least one additional targeting molecule. The additional target molecule site comprising the poly amine-acid subunit is envisioned to play several roles. The additional target molecule site can function to enhance specificity of targeting, broadening targeting to multiple sites in the body or expanding treatment modalities. In one application, the additional targeting molecule functions to enhance discrimination of the disease cell over healthy cells. In another application the additional targeting molecule provides for delivery of the vehicle to two different tissues, cells or organs. In another application the additional target molecule site comprising the vehicle can provide clinicians and their patients more delivery options (e.g. oral, injectable, implantable, inhalation ect.)

The targeted drug delivery vehicle can be further enhanced by a modifications (e.g. biochemical or chemical modifications) which can improve the properties of the drug delivery vehicle. A For example, the targeting amino acid chain can be modified by associating a molecule with an aliphatic chain of the targeting amino acid chain.

The targeting amino acid chain can be further enhanced by the attachment of a modifications. For example the invention provides for the biochemical modification by an aliphatic chain. The aliphatic chain can be associated with the targeting amino acid chain using various methods, for example by association through van der Waals forces or by ionic bonding conjugation. Alternatively, conjugation of the aliphatic chain to the α-helix amino acid can be accomplished using covalent bonding. The invention provides for compositions to include a stoichiometry of one or more aliphatic chains to a targeting amino acid molecule. By way of example an amino-acid component can be comprised of 1:1 aliphatic chains: targeting amino acid chain sor 1:2 or 1:3 or 1:4. Suitable aliphatic chains to be used with the amino-acid composition include, but are not limited to, fatty acids, glycerolipids, glycerophospholipids, sphingolipids, sterol lipids, saccharolipids and polyketides.

Fatty acids are aliphatic chains that are comprised of carboxylic acid with either saturated or unsaturated chain(s) of hydrocarbons. Unsaturated fatty acids have one or more double bonds between carbon atoms owing to a lack of a hydrogen atom. Some examples of unsaturated fatty acids include, but are not limited to, myristoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid.

Saturated fatty acids are long-chain carboxylic acids that usually have between 12 to 24 carbons in length and have no double bonds. Examples of saturated fatty acids include, but are not limited to, caprylic acid, capric acid, lauric acid, myristic acid, palmitic acid, stearic acid, arachidic acid, behenic acid, lignoceric acid, and cerotic acid.

Most naturally occurring fatty acids are comprised of a chain of carbons ranging from 4 to 28 carbons in length. Fatty acids can be categorized as short-chain, medium-chain, long-chain, very-long fatty acid chain. Short-chain fatty acids are fatty acids with aliphatic tails comprised of fewer than 6 carbons in length. Medium-chain fatty acids are defined as fatty acids with aliphatic tails comprised of 6 to 12 carbons in length. Long-chain fatty acids are fatty acids with aliphatic tails comprised of longer than 12 carbons in length. Very long chain fatty acids are defined as fatty acid comprised of tails with more than 22 carbons in length. In one embodiment of the composition, the aliphatic chain is one or more short-chain, medium-chain, long-chain, or very long fatty acid chain(s). In another composition of the invention, the aliphatic chain attached to the poly amine-acid is less than 15 carbons in length but no shorter than 3 carbons in length.

Glycerolipids are composed mono-, di-, and/or tri-substituted glycerols. Additional subclasses of glycerolipids are represented by glycosylglycerols. Glycosylglycerols are characterized by the presence of one or more sugar residues attached to glycerol via a glycosidic linkage. In another composition of the invention, the aliphatic chain attached to the poly amine-acid is one or more glycerolipids.

Glycerophospholipids, usually referred to as phospholipids are key components of the lipid bilayer of cells and are also involved in metabolism and cell signaling events. Examples of glycerophospholipids include, but are not limited to, phosphatidylcholine, phosphatidylethanolamine, phosphatidylserine phosphatidylinositols and phosphatidic acids. In one composition of the invention, the aliphatic chain attached to the poly amine-acid is one or more glycerophospholipids that is not a palmitoyl-oleyl phosphatidylcholine.

Sphingolipids are comprised of a sphingoid base backbone. Sphingolipids play important roles in signal transmission and cell recognition. The main mammalian sphingoid bases found in mammals are dihydrosphingosine and sphingosine. Examples of sphingolipids include, but are not limited to, ceramides with an amide-linked fatty acid and ceramide phosphocholines. In another composition of the invention, the aliphatic chain attached to the poly amine-acid is one or more sphingolipids.

Sterol lipids all derived from the same fused four-ring core structure. They are important component of membrane lipids have different biological roles as hormones and signaling molecules. Example of sterol lipids include, but are not limited, to cholesterol and its derivatives, estrogen testosterone, androsterone, progestogens, glucocorticoids, mineralocorticoids, and bile acids. In another composition of the invention, the aliphatic chain attached to the poly amine-acid is one or more sterol lipids which are not unesterified cholesterol.

Saccharolipids are another type of aliphatic chains in which the fatty acids chains are directly linked to a sugar backbone. Saccharolipids are compatible with membrane bilayers. In another composition of the claimed invention, the aliphatic chain attached to the poly amine-acid is one or more saccharolipids.

Polyketides are another type of aliphatic chains that are synthesized by polymerization of acetyl and propionyl subunits. The polyketides family exhibits great structural diversity. In another composition of the claimed subunit, the aliphatic chain attached to the poly amine-acid is one or more polyketides.

In another aspect of the invention, the targeting amino acid chain can be further enhanced by other natural occurring protein chemical modifications that would enhance or retain its natural affinity to its target which is complexes with. Examples of suitable chemical modifications that can be used with the claimed invention include, but are not limited to, acetate, phosphate, various lipids and carbohydrates and equivalents. In another composition of the claimed subunit, the poly amine-acid includes one or more biochemical modifications including, but not limited to, acetate, phosphate, various lipids and/or carbohydrates.

Drug Delivery Vehicle

While lipoproteins have been envisioned to be suitable drug delivery vehicles, the clinical application of these vehicles has faced both commercialization and technical hurdles. Commercial scale production has been prohibited owing to the difficulty of obtaining large quantities of purified biomaterials and the complexity of steps employed to produce the vehicle. In addition, lipoprotein based vehicles also face several technical challenges such as stability in the body fluids and limited payload capacity. The present invention overcomes these previous challenges.

The present application provides for a biocompatible targeted drug delivery vehicle composition. In one embodiment the targeted drug delivery vehicle is the assembly of multiple targeting amino acid chains compositions into a drug delivery vehicle composition. The targeted drug delivery vehicle can have a substantially spherical shape and a size range about 20 nm to 100 nm in diameter (FIG. 1). The targeted drug delivery vehicle can have a largely a hydrophobic core and hydrophilic exterior. The hydrophobic portions can function as "cargo space" allowing for both the loading and containment of pharmaceutical agents prior to the delivery of the pharmaceutical agents to the targeted cell, tissue or organ type.

The number of targeting amino acid chains used to comprise the targeted drug delivery vehicle is expected to vary slightly, as its ultimate size will be dependent on the type of drug and the amount of drug that is to be associated or encapsulated by the claimed vehicle. It will be obvious to those skilled in the art what will be a sufficient number of subunit molecules to form the spherical vehicle, based on conformation and integrity assessments using such methods as C-D spectrometry, atomic force microscopy, transmission electron microscopy, scanning electron microscopy or equivalent methods.

By way of example the invention provides for drug delivery vehicle compositions that can be comprised of about 5 to 10 targeting amino acid chains, 10 to 15 targeting amino acid chains, 15 to 20 targeting amino acid chains, 20 to 25 targeting amino acid chains 30 to 35 targeting amino acid chains, 35 to 40 targeting amino acid chains, 40 to 45 targeting amino acid chains, or 45 to 50 targeting amino acid chains or 50 to 55 targeting amino acid chains or 55 to 60 targeting amino acid chains.

The invention also provide for the vehicle to be free of unesterified cholesterol, esterified cholesterol, phospholipids, including phosphatidylcholine, phosphatidyl serine, phosphatidyl inositol, phosphatidyl ethanolamine, diphosphoglyceride, folic acid or the apo A-1 protein or a portion of apo A-1 protein greater than 50 amino acids in length.

An additional aspect of the claimed targeted drug delivery vehicle composition is enhanced stability in fluids as compared to passive drug delivery and phospholipid based delivery vehicle. As the phospholipid-based vehicles come in contact with body fluids, their lipid curvature increases and resulting in destabilization of their structure. This destabilization compromises the vehicles integrity, and ultimately results in the leakage of the drug out of the vehicle prior to delivery. The claimed invention offers improved bioavailability over both conventional passive drug delivery methods and phospholipid-based drug delivery vehicles, by providing better stability and protection from inactivation by the biological environment, and as a result of theses properties, the claimed invention ultimately provides more accurate drug dosing to the site of disease.

Figure 3:
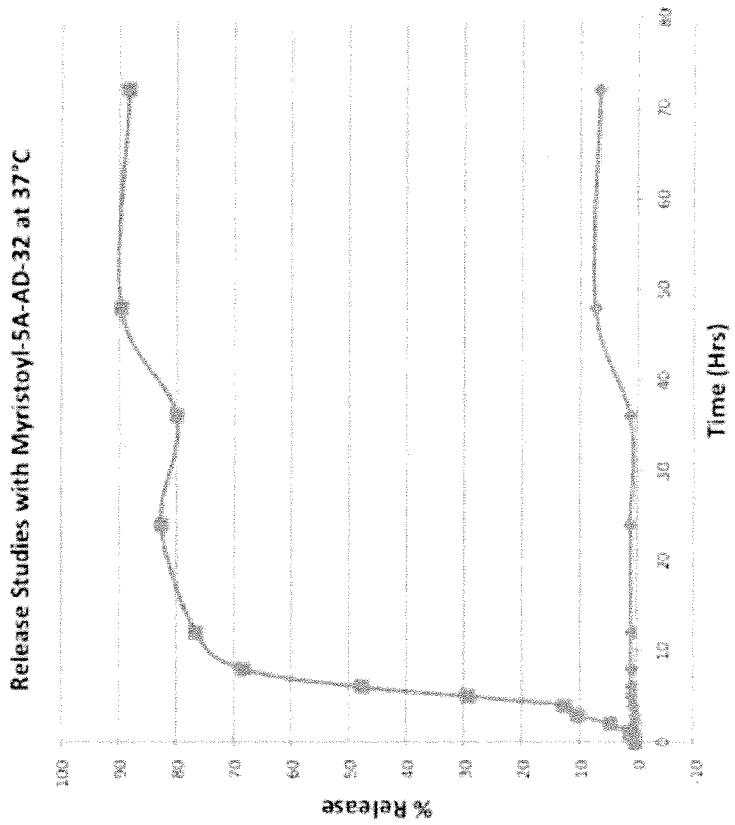
FIG. 3 shows comparative in vitro dissolution studies of drug-loaded vehicle compared to conventional passive drug delivery using dynamic dialysis technique to determine in vitro release in PBS at 37° C. 92% of originally concentration of drug loaded in the vehicle was maintained after 72 hours incubation. For passive drug delivery, 70% of the original concentration was released within 8 hours of incubation.
Figure 4:
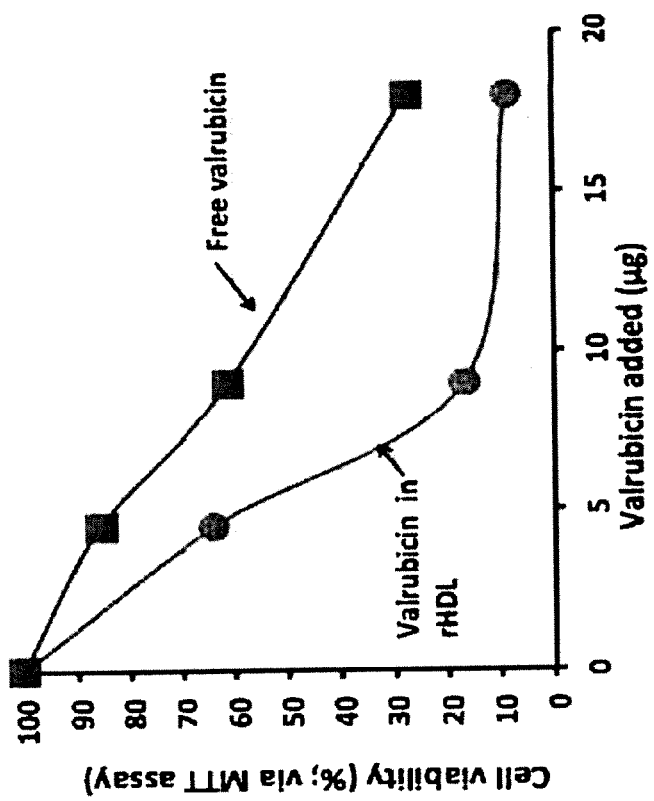
FIG. 4 shows dose-response comparative studies determining the half maximal inhibitory ($IC_{50}$) concentration values of valrubcin (N-trifluoroacetyladriamycin-14-valerate) in the ovarian cell cancer model SKOV-3 (HTB-77) drug-loaded vehicle compared to conventional passive drug delivery. The vehicle delivery drug has an $IC_{50}$ of less than 6 μg and passive drug delivery had an IC50 greater than 12 μg, illustrating that the vehicle delivery has a 2-fold enhancement of cytotoxicity over passive drug delivery.

Another aspect of the vehicle composition is increased time of dissolution relative to passive drug delivery (FIG. 3). The vehicle compositions of the invention provides for a drug vehicle with a dissolution profile in which within about 5 minutes at least about 20% of the therapeutic agent is dissolved. In other embodiments of the invention, at least about 30% or at least about 40% of the therapeutic agent is dissolved within about 5 minutes. In yet other embodiments of the invention, preferably at least about 40%, at least about 50%, at least about 60%, at least about 70%, or at least about 80% of the therapeutic agent is dissolved within about 10 minutes. Finally, in another embodiment of the invention, preferably at least about 70%, at least about 80%, at least about 90%, or at least about 100% of the therapeutic agent is dissolved within about 20 minutes.

Figure 7:
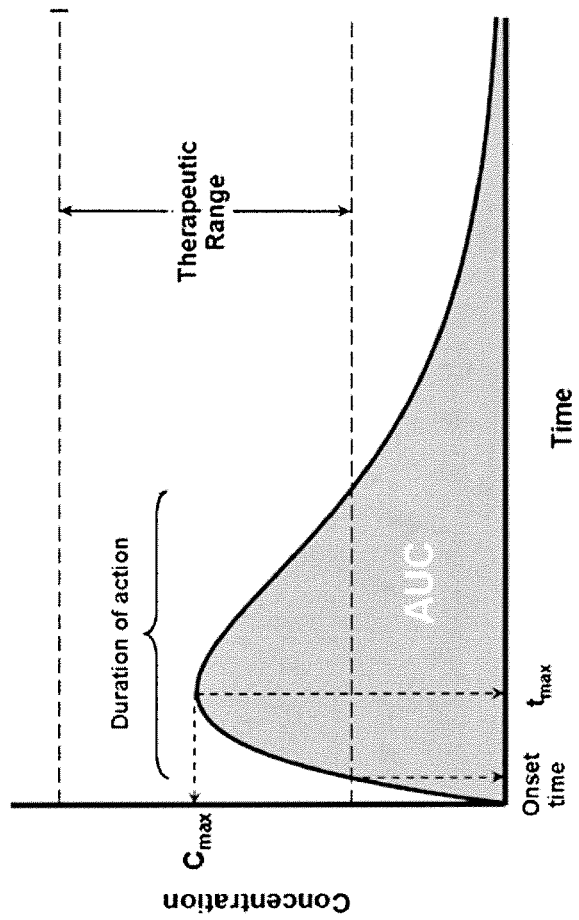
FIG. 7 shows comparative pharmacokinetic profile studies with the drug delivery vehicle versus passive drug delivery.

The claimed drug delivery vehicle composition exhibits plasma concentration profiles that shows an increased in maximal drug delivery concentration relative to conventional passive drug delivery. By way of non-limiting example, a desirable pharmacokinetic profile of the composition could include a $C_{max}$ for therapeutic agent when assayed in the plasma of a subject following administration that is preferably greater than the $C_{max}$ for the same therapeutic agent when delivered at the same dosage by conventional passive drug delivery or an AUC for therapeutic agent when assayed in the plasma of a subject following administration that is preferably greater than the AUC for the same agent when delivered at the same dosage by conventional passive drug delivery; or a $T_{max}$ for therapeutic agent when assayed in the plasma of a subject following administration that is preferably less than the $T_{max}$ for the same therapeutic agents when delivered at the same dosage by conventional passive drug delivery (FIG. 7).

The targeted drug delivery vehicle compositions can exhibit a plasma concentration profile that shows an increase maximum concentration drug delivery time relative to conventional passive drug delivery. In some applications of the claimed composition vehicle composition exhibits, for example, a $T_{max}$ for therapeutic agents or equivalents, contained therein which is not greater than about 90% of the $T_{max}$ for the same agent and dosage delivered by a with conventional passive drug. In other embodiments the particulate composition may exhibit, for example, a $T_{max}$ for therapeutic agent, which is not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the $T_{max}$ for the same agent and dosage delivered by a with conventional passive drug. The $T_{max}$ of the claimed vehicle will vary depending on the target site and vehicle size. By way of example only, in one embodiment of vehicle composition will exhibit a $T_{max}$ of the therapeutic agent delivered by the claimed vehicle when assayed in the plasma of the subject is less than about 6 to about 8 hours, less than about 6 hours, less than about 5 hours, less than about 4 hours, less than about 3 hours, less than about 2 hours, less than about 1 hour, or less than about 30 minutes after administration.

Another aspect of the targeted drug vehicle composition can exhibit a plasma concentration profile that shows an increased AUC relative to passive drug delivery allowing for better steady state dosage levels. The invention provides for vehicle a composition that exhibits, for example, an AUC for a therapeutic agent which is at least about 25% greater than the AUC for the same therapeutic and dosage when delivered by passive conventional drug delivery. Other vehicle composition may exhibit, for example, an AUC for therapeutic agent which is at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC for the same therapeutic and dosage delivery by passive conventional drug delivery.

Figure 9:
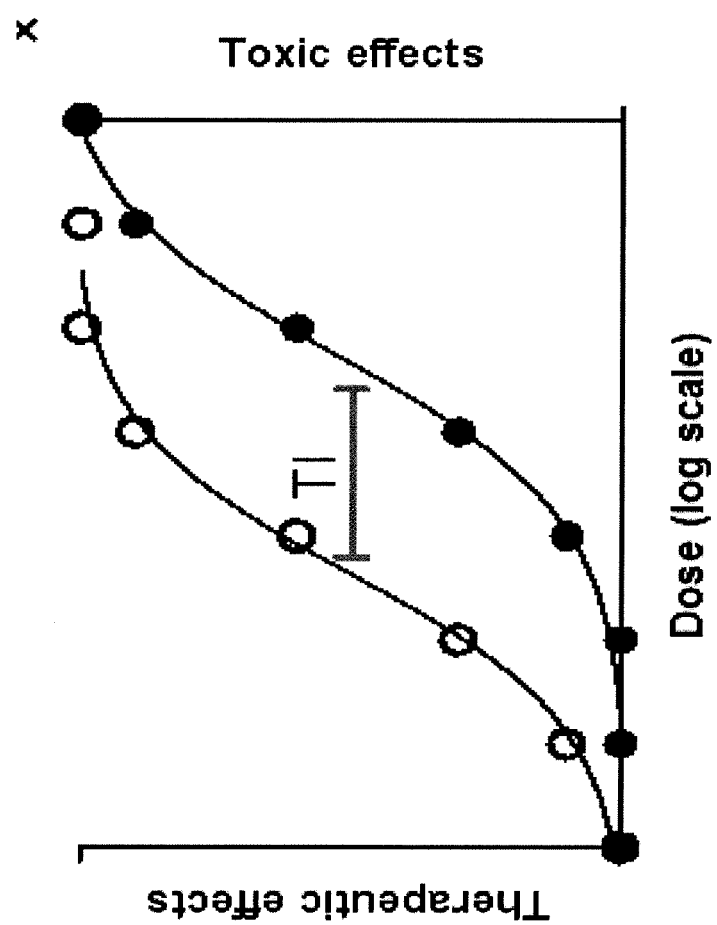
FIG. 9 shows therapeutic index study with the drug delivery vehicle and passive drug delivery.
Figure 10:
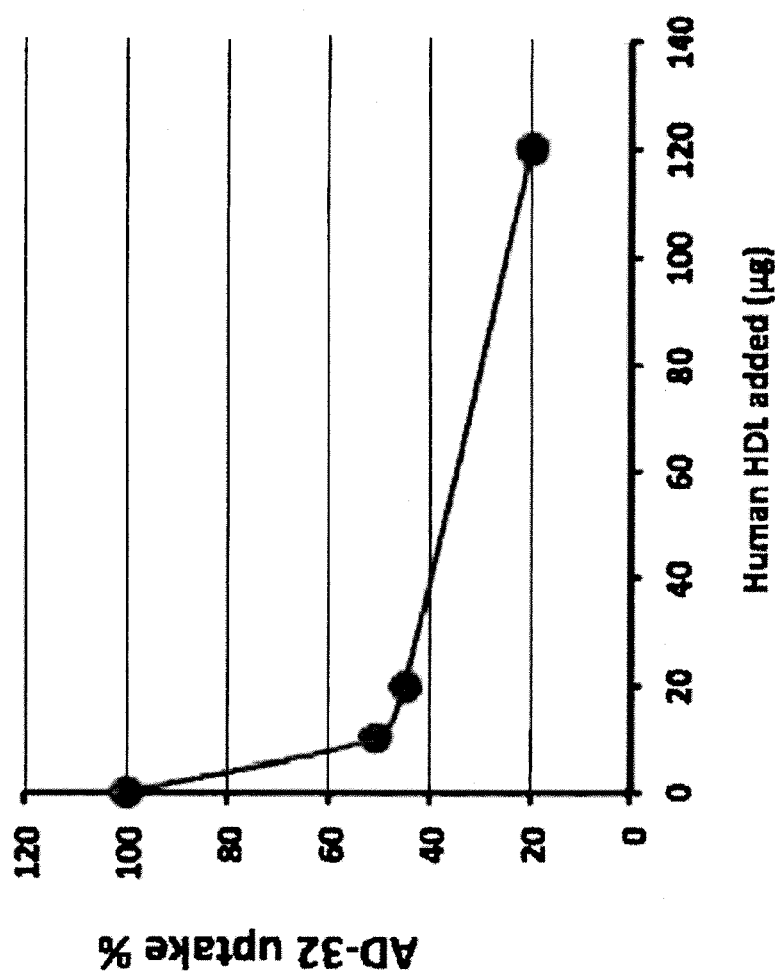
FIG. 10 shows competition study for the HDL receptor by the drug delivery vehicle and increasing amounts of HDL.

The therapeutic index is the ratio of the amount of a therapeutic agent that causes the therapeutic effect to the amount that causes death (in animal studies) or toxicity (in human studies). The therapeutic index ratio is calculated by the lethal or toxic dose divided by the therapeutic dose. A therapeutic agent with a narrow therapeutic range (i.e. having little difference between toxic and therapeutic doses) may have its dosage adjusted according to measurements of the actual blood levels achieved in the person taking it. A higher therapeutic index is preferable to a low therapeutic index; a patient would have to take a much higher dose to reach the lethal/toxic threshold than the dose taken to elicit the therapeutic effect. The invention provides for a composition that increases the therapeutic index of therapeutic agents greater than 20%, greater than 30% greater than 40% greater than 50%, greater than 60% relative to the therapeutic index of the same drug delivered by conventional passive drug delivery (FIG. 9).

One problem during a cancer chemotherapy regimen, is the phenomenon called drug resistance. Drug resistance occurs when the cancer cells that initially were suppressed by anticancer drug treatment, develop resistance to the drug over time. This is caused primarily by reduced drug uptake (in the cell) and increased drug efflux (out of cell). In addition, chemotherapeutic agents often have a narrow therapeutic index window. It is envisioned that the claimed drug delivery vehicle, will function to reduce drug resistance when treating patients with chemotherapeutic drugs due to the direct delivery of the encapsulated drugs into the cell's cytoplasm and thus limiting the exposure to the membrane localized drug resistance pumps.

Therapeutic Agents

The claimed vehicle can be associated with broad categories of therapeutic agents having diverse physical properties. Suitable drugs envisioned to be associated with the claimed targeted drug delivery vehicle include, but are not limited to, heparin, low-molecular-weight heparin, heparinoids such as dextran sulfate and beta-cyclodextrin tetradecasulfate, heparin derivatives, urokinase, RGD peptide-containing compound, antithrombin compounds such as hirudin, hirulog, and argatrob an, platelet receptor antagonists, antithrombin antibodies, antiplatelet receptor antibodies, aspirin, prostaglandin inhibitors and antiplatelet peptides, GPIIb and IIIa inhibitors such as ticlopidine, clopidogrel, abciximab, eptifibatide, and tirofiban, FXa inhibitors, anticoagulants such as vitamin K inhibitors (e.g., warfarin), antithrombotic agents, platelet agents, platelet adhesion inhibitors such as albumin and polyethylene oxide, cyclooxygenase pathway inhibitors such as aspirin, ibuprofen, flurbiprofen, indomethacin, and sulfinpyrazone, lipoxygenase pathway inhibitors, leukotriene receptor antagonists, thromboxane A2 (TAX2) pathway modifiers such as sulotroban, vapiprost, dazoxiben, and ridogrel, natural and synthetic adrenal cortical steroids such as dexamethasone, prednisolone, corticosterone, methoprednisolone, and hydrocortisone, estrogen, anti-inflammatory drugs (e.g., sulfasalazine and mesalamine), antitumor agents, antiproliferative drugs, mitotic division inhibitors, cell-division-arresting agents, and cell-proliferation-influencing factors (e.g., paclitaxel, 5-fluorouracil, cisplatin, vinblastine, vincristine, epothilone, endostatin, angiostatin, angiopeptin, monoclonal antibodies capable of blocking smooth muscle cell proliferation, and thymidine kinase inhibitors), cell cycle inhibitors such as CDK inhibitors, tyrosine kinase inhibitors (e.g., tyrphostin, genistein, and quinoxaline derivatives) and other protein kinase inhibitors, purine analogs (cladribine that is a 6-mercaptopurine or chlorinated purine nucleotide analog), metabolic antagonists such as pyrimidine analogs (e.g., cytarabine and 5-fluorouracil) and methotrexate, antitumor antibiotics such as nitrogen mustard, alkyl sulfonic acid, ethyleneimine, daunorubicin, and doxorubicin, drugs that influence microtubule movement such as nitrosourea, cisplatin, vinblastine, vincristine, colchicine, paclitaxel, and epothilone, angiogenesis inhibitors such as caspase activators, proteasome inhibitors, endostatin, and angiostatin, antiproliferative and antitumor agents (e.g., rapamycin, cerivastatin, flavopiridol, and suramin), vascular cell growth inhibitors such as growth factor inhibitors, growth factor receptor antagonists, antibodies antagonistic to growth factors, transcription repressors, translation repressors, replication inhibitors, antibodies capable of recognizing endothelial progenitor cells, bifunctional molecules comprising growth factors and cytotoxin, and bifunctional molecules comprising antibodies and cytotoxin, cytokine and hormone, acidic and basic fibrous cell growth factors, FGF pathway drugs such as bFGF antibodies and chimeric fusion proteins, angiogenesis factors such as growth factors (e.g., angiopoietin, vascular endothelial growth factors, endothelial division promotion (growth) factors, epithelial growth factor, transforming growth factors alpha and beta, platelet-derived endothelial growth factors, platelet-derived growth factors, tumor necrosis factor alpha, hepatocellular growth factors, and insulin-like growth factors), endothelialization-promoting agents such as RGD peptide, PDGF receptor antagonists such as trapidil, IGF pathway drugs such as somatostatin analogs (e.g., angiopeptin and octreotide), polyanion reagents (e.g., heparin and fucoidan), TGF-beta pathway drugs such as decorin and TGF-beta antibodies, EGF pathway drugs such as EGF antibodies, TNF-alpha pathway drugs such as receptor antagonists, chimeric fusion proteins, and thalidomide and analogs thereof, adenylate and guanylate cyclase stimulants such as forskolin, cyclic nucleotide pathway drugs such as phosphodiesterase inhibitors (e.g., cilostazol and dipyridamole), calcium channel blockers such as benzothiazepine (e.g., diltiazem), dihydropyridine (e.g., nifedipine, amlodipine, and nicardipine) and phenylalkylamine (e.g., verapamil), serotonin pathway modifiers such as 5-HT antagonists (e.g., ketanserin and naftidrofuryl) and 5-HT absorption inhibitors (e.g., fluoxetine), catecholamine modifiers such as alpha antagonists (e.g., adenosine analogs, prazosin, and bunazosin), beta antagonists (e.g., propranolol), and alpha and beta antagonists (e.g., labetalol and carvedilol), endothelin receptor antagonists, ACE inhibitors such as cilazapril, fosinopril, and enalapril, endogenous vasoactive mechanism inhibitors such as angiotensin-receptor antagonists (e.g., saralasin, losartan, candesartan, and valsartan), other vasodilators such as hydralazine, adrenaline a agonists, adrenaline beta agonists, dopamine agonists, prostaglandins, analogs thereof, and prostacyclin analogs such as prostaglandins E1, E2 and I2, organic nitrates and nitrites such as nitroglycerin, isosorbide dinitrate, and amyl nitrite, inorganic nitroso compounds such as sodium nitroferricyanide(III) dehydrate, sydnonimines such as molsidomine and linsidomine, nitrogen monoxide adducts such as diazeniumdiolate and alkanediamine, S-nitroso compounds containing low-molecular-weight compounds (e.g., S-nitroso derivatives of captopril, glutathione, and N-acetylpenicillamine) and S-nitroso compounds containing high-molecular-weight compounds (e.g., S-nitroso derivatives of proteins, peptides, oligosaccharides, polysaccharides, synthetic polymers, or oligomers and natural polymers or oligomers), nitrogen monoxide donors and nitrogen monoxide-releasing molecules such as C-nitroso compounds, O-nitroso compounds, N-nitroso compounds, and L-arginine, E- and P-selectin antagonists, VCAM-1-ICAM-1 interaction inhibitors, macrophage activation inhibitors such as bisphosphonate, cholesterol-lowering agents such as HMG-CoA reductase inhibitors (e.g., lovastatin, pravastatin, fluvastatin, simvastatin, cerivastatin, and pitavastatin), fish oil and omega-3-fatty acid, radical scavenger antioxidants such as probucol, vitamins C and E, ebselen, and trans retinoic acid, anesthetic drugs such as lidocaine, bupivacaine, and ropivacaine, MMP pathway inhibitors such as marimastat, ilomastat, and metastat, cell movement inhibitors such as cytochalasin B, matrix deposition and assembly pathway inhibitors such as quinazolinone derivatives (e.g., halofuginone) and tranilast, hemorheology modifiers such as pentoxifylline, triclosan, antimicrobial agents such as nitrofurantoin, penicillin antibiotics such as sultamicillin, amoxicillin, aspoxicillin, and piperacillin, cephalosporin antibiotics such as cefaclor, cefazolin, cefotiam, flomoxef, cefteram, ceftazidime, cefmenoxime, cefozopran, and cefsulodin, carbapenem antibiotics such as imipenem, panipenem, and meropenem, monobactam antibiotics such as aztreonam, aminoglycosides such as amicacin, dibekacin, tobramycin, teicoplanin, streptomycin, and gentamicin, synthetic antimicrobial agents such as polymixin B, vancomycin, nalidixic acid, ofloxacin, ciprofloxacin, tosufloxacin, levofloxacin, and fosfomycin, macrolide antibiotics such as erythromycin, clarithromycin, roxithromycin, and azithromycin, lincomycin antibiotics such as clindamycin and lincomycin, tetracycline antibiotics such as doxycycline and minocycline, antibiotics and antimicrobial agents such as chloramphenicol, thiamphenicol, sulfurmethoxyn, and sulfurmethoxazole, antituberculous agents such as isoniazid, rifampicin, and ethambutol, antileprotics such as diaphenylsulfone and clofazimine, antifungal agents such as nystatin, miconazole, metronidazole, fluconazole, amphotericin B, and clotrimazole, antiviral agents such as ganciclovir, oseltamivir, vidarabine, aciclovir, and palivizumab, and antiprotozoal agents such as pentamidine.

The targeted drug delivery vehicle composition provides increased solubilization of a drug when associated with the delivery vehicle. Accordingly, the solubility of the drug is greater when associated with the vehicle than when it is (free) not associated with the vehicle. In one application, the solubility of hydrophobic drugs is greater when associated with the vehicle and thus remains solubilized prior to delivery of the drug into the cell. One aapplication, the solubility of hydrophilic drugs is greater associated with the vehicle and remains solubilized prior to delivery of the drug into the cell. In another application of the invention, the solubility of macromolecular compounds drugs is greater associated with the vehicle and remains solubilized prior to delivery of the drug into the cell. In another embodiment of the invention, the solubility of small molecule compounds drugs is greater associated with the vehicle and remains solubilized prior to delivery of the drug into the cell.

In another embodiment, the invention provides a targeted drug delivery vehicle comprising multiple targeted poly amino-acid subunits, wherein each targeted poly-amino-acid subunit contains a polynucleotide, a phospholipid, an excipient, and a targeting amino acid chain. The polynucleotide may be in the range of about 500-2500 kilobases. In one example, the phospholipid may be phosphatidylcholine and the peptide may be an apolipoprotein A-I (apo A-I) mimetic. The peptide in this embodiment may be between about 18 and 38 amino acids in length, and the complex may be between about 300-1000 nm in diameter. The polynucleotide may be neutralized with a positively charged chemical via suppression of its (native) negative charges before incorporation into the nanoparticle assembly. In this embodiment, the bioavailability of the enclosed polynucleotide is enhanced compared with polynucleotide alone, and the therapeutic benefits of the polynucleotide are enhanced compared with polynucleotide alone when administered to animals or humans.

The study of disease etiology has discovered that a large portion of disease is caused by dysregulation of genetic factors. As a result, a growing area of therapeutics is gene therapeutic technology. One aspect of gene therapeutic technology is based on gene-silencing therapies using RNA interference (RNAi) or antisense (RNAa) technologies. Antisense or RNAi nucleic acids are designed to specifically bind to targeted nucleic acids, resulting in the formation of RNA-DNA or RNA-RNA hybrids, which function to silence or reduce of the expression of the targeted gene. Gene expression is reduced through various mechanisms including an arrest of DNA replication, transcription or/and translation of messenger RNA (mRNA).

RNAa is a single-stranded RNA that is complementary to an mRNA strand transcribed within a cell. Once in the cell, antisense inhibits translation by base pairing the complementary RNA and physically obstructing the translation machinery. In date, fomivirsen, used in the treatment of cytomegalovirus retinitis, is the only antisense therapeutic on the market. One hurdle to the development of antisense therapeutic has been lack of means for efficient administration. It is envisioned that the claimed vehicle is associated with RNAa therapeutics, for example fomivirsen and its equivalents thereof.

RNAi agents targeting the sequence causing the disease can be prepared according to any of a number of methods that are known in the art, including in vitro and in vivo methods, as well as by synthetic chemistry approaches. RNAi sequences do not exceed about 100 nucleotides (nt) in length, and typically does not exceed about 75 nt in length, where the length in certain embodiments is less than about 70 nt. Where the RNAi agent is a duplex structure of two distinct ribonucleic acids hybridized to each other, the length of the duplex structure typically ranges from about 15 to 30 base pairs (bp) usually from about 15 to 29 bp, where lengths between about 20 and 29 bp and more preferably, (e.g., 21 bp, 22 bp). Where the RNAi agent is a duplex structure of a single ribonucleic acid that is present in a hairpin formation, the length of the hybridized portion of the hairpin is typically the same as that provided above for the RNAi type of agent or longer by 4 to 8 nt. RNAi therapeutics can be engineered with certain chemical modifications for stability and conjugation for delivery.

One of the hurdles facing RNAi therapeutics for implementation as a mainstream therapeutic is its potential for "off-target" effects, that is, its propensity to repress other non-targeted genes with similar sequence to the targeted gene. One way to reduce the "off-target" effect of RNAi therapeutics is to have targeted delivery of the RNAi therapeutic to the disease cell. It is envisioned that the claimed vehicle is associated with RNAi therapeutics or equivalents thereof.

In one embodiment, the gene-silencing agent is an antisense that acts to reduce expression of the targeted sequence causing the disease. In another embodiment of the invention the gene-silencing is a small interfering double or single stranded RNAs (RNAi) sequence that acts to reduce expression of the targeted sequence causing the disease. The invention provides for a method of treatment using gene therapeutics associated with the claimed vehicle and administered alone or in conjunction with an admixture of one or more additional therapeutic agents to a patient suffering from a diseases caused, in part, by the gene targeted for silencing.

Produgs are therapeutic agents that can be activated by an enzyme, chemical or physiological stimuli to release the active drug from the chemically-constraining portion. Suitable prodrugs that can be used with the invention include type I and type II and subtypes thereof. Non-liming examples of prodrugs include, type I prodrugs which are bioactivated intracellularly, type II prodrugs which are bioactivated extracellularly, type IA prodrugs include many antimicrobial and chemotherapy agents (e.g., 5-fluorouracil), type IB agents rely on metabolic enzymes, especially in hepatic cells, to bioactivate the prodrugs intracellularly to active drugs, type IIA prodrugs are bioactivated extracelluarly, either in the milieu of GI fluids, type IIB within the systemic circulation and/or other extracellular fluid compartments or type IIC near therapeutic target tissues/cells relying on common enzymes such as esterases and phosphatases or target directed enzymes and mixed-type prodrugs. Mixed-type prodrugs can belong to multiple subtypes classes (e.g. is bioactivated at multiple sites, either in parallel or sequential steps). By way of example only, a mix-type prodrug is bioactivated concurrently in both target cells and metabolic tissues (e.g., HMG Co-A reductase inhibitors and some chemotherapy agents). Currently, proteases are considered an important target for development of prodrugs because proteases are highly involved in diseases.

In one embodiment, the invention can be applied with a two-step delivery of vehicle carrying the prodrug-activating enzyme and another vehicle carrying the prodrug to be activated. After the two vehicles release their cargo inside the target cell, the prodrug-activating enzymes can then bioactivate the prodrug ensuring that the majority of the prodrug will be activated inside the cell.

Methods

A. Manufacture of Drug Delivery Vehicle

Figure 2:
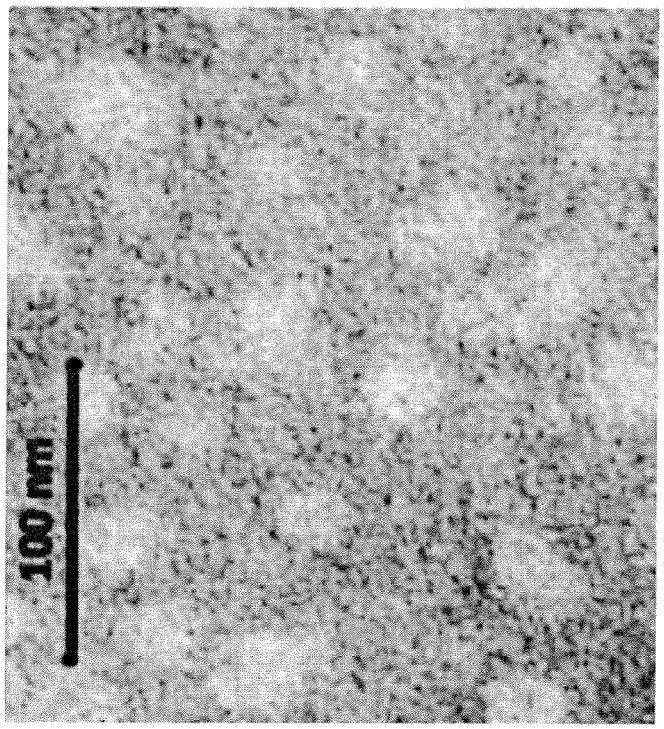
FIG. 2 shows a transmission electron microscopy image illustrating substantially spherical shape of a drug delivery vehicle containing the chemotherapeutic, paclitaxel with a mean diameter of ~20 nm.
Figure 6:
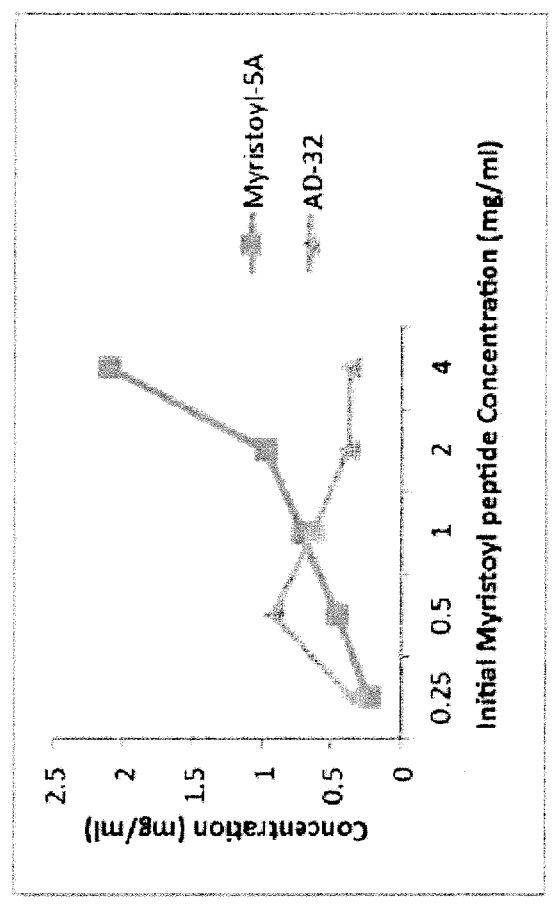
FIG. 6 (A) shows drug loading capacity studies (B) shows drug loading efficiency studies with vehicle comprising increasing concentrations of SEQ ID NO:20-myr component.

In another aspect, the invention features a method of manufacturing the drug delivery vehicle containing a drug. One of the advantages of the claimed composition is that the subunit composition readily coalesces into vehicle with highly homogenous architecture and high loading efficiency (FIGS. 2 and 6). These features allows, along with the synthetic nature of the materials comprising the vehicle, allows for manufacturing at a commercial scale level.

The vehicle can be loaded with a drug using several different techniques. The vehicle can be loaded with a drug during constitution the vehicle such that the drug becomes encapsulates during the synthesize from its parts. This can be accomplished via turbulent mixing, sonication, vibrational atomization, and continuous flow mixers, rapid mixing using the solvent displacement method, cholate dialysis and other methods.

Sonication can be used to constitution the vehicle by mixing two liquid streams. One stream contains the dissolved vehicle polymeric material and the second stream contains a drug and/or combination of drugs. At the point of stream intersection, an inline ultrasonic vibrating plate will cause the vehicle to come out of solution and solidify. It is envisioned that the claimed vehicle is manufactured using sonication methods as described or similar variations.

Vibrational atomization can also been used to form liquid droplets for vehicle manufacture. Such devices as DMP-2800 MEMS-based piezoelectric micropump (inkjet) system produced by the Spectra Printing Division (Lebanon, N.H.) of Dimatix, Inc. (Santa Clara, Calif.) forms a 10-50 pL (1-5.times.10.sup.-11 liter) sized liquid droplet at 100,000 pL/s. Micropumps (inkjet systems) offer uniform mixing. It is envisioned that the claimed vehicle is manufactured using vibrational atomization methods described or similar variations.

One could also use continuous flow mixers to make the vehicle containing drugs. Various mixers have been developed that provide turbulent mixing on a sub-millisecond timescale. Examples of such mixing devices include, but are not limited to, modified T-mixers, for example, the Berger mixer or the Wiskind mixer (R. L. Berger, B. Balko and H. F.

Chapman in Rev. Sci. Instrum., 39:493-498 (1968) and R. E. Hansen and M. W. Tonsager in J. Phys. Chem., 92:2189-2196 (1988). The Wiskind mixer has a proven ability to achieve homogeneous mixing of two or more fluid streams during passage through the mixer. This system has been shown to be effective for the manufacturing of vehicles less than 100 nm and would allow for industrial scale production and therefore would allow for the development of a commercial scale production process. It is envisioned that the claimed vehicle is manufactured using flow mixers methods described or similar variations.

One could also make the vehicle of the claimed invention using rapid mixing using the solvent displacement method. In some such embodiments, a stirring rate of 500 rpm or greater is typically employed. Slower solvent exchange rates during mixing result in larger vehicle. Fluctuating pressure gradients are used to produce high Reynolds numbers and efficient mixing in fully developed turbulence. Use of high gravity reactive mixing has produced small vehicles (10 nm) by achieving centrifugal vehicle acceleration similar to that achieved by turbulent mixing at high Reynolds numbers. It is envisioned that the claimed vehicle is manufactured associated with the drug using solvent displacement methods described or similar variations.

One could also make the vehicle of the claimed invention using sodium cholate dialysis. Sodium cholate (cholic acid) is a water soluble bile acid. The drug (Paclitaxel, 2 mg) in DMSO is dried to a thin film under $N_2$. Subsequently, 50 µl of the Myristoyl 5A peptide solution (10 mg/ml-in D.I. water) is added. 14 mg of sodium cholate is added from a 100 mg/ml stock solution. The mixture is brought to a total volume of 2 ml with 10 mM Tris, 0.1M KCl, 1 mM EDTA pH 8.0. The mixture is incubated overnight at 4° C. and subsequently dialyzed against 2 liters of PBS (0.15M NaCl, 0.003M KCl, 0.15M $KH_2PO_4$, pH 7.4) with 4 changes of buffer during 48 hrs. Using $^3H$-cholate as a tracer, <2% of the cholate remained in the sHDL/drug preparations while over 60% of the paclitaxel remained associated with the sHDL delivery vehicle.

Other methods envisioned to make the vehicle include vaporization methods (e.g., free jet expansion, laser vaporization, spark erosion, electro explosion and chemical vapor deposition), physical methods involving mechanical attrition (e.g., the pearl milling technology developed by Elan Nanosystems of Dublin, Ireland), and interfacial deposition following solvent displacement.

Alternatively, the drug can be covalently bound to the vehicle. Typical amino acids used for the conjugation site include, but are not limited to, lysine, arginine, tyrosine, and cysteine residues. The drug can be either conjugated to the surface of the vehicle or onto the head group of the alphatic tail (e.g. fatty acid). It is envisioned that the claimed vehicle is associated to the drug using covalent bond conjugation methods as described or similar variations.

The vehicle can be loaded with a drug also using inculcation methods. Drugs, having a degree of amphiphilicity, can be inculcated within the surface of the vehicle through non-covalent interactions, such as, van der Waals forces. It is envisioned that the claimed vehicle is associated with the drug using inculcation methods described or similar variations. Alternatively, the claimed vehicle is manufactured associated with the drug using inculcation method combined in concert with cholate dialysis techniques.

One could load the vehicle with hydrophobic drugs via reconstitution techniques. This technique exchanges the hydrophobic with the desired hyrdrophobic drug by lyophilization and organic extraction. It is envisioned that the claimed vehicle is manufactured associated with the drug using reconstitution techniques methods described or similar variations.

B. Delivery Methods

The present invention provides for methods of treating a patient with the claimed vehicle associated with a therapeutic-effective amount of a pharmaceutical agent. Suitable routes of administration include, but are not limited to, non-invasive peroral (through the mouth), transmucosal (nasal, buccal/sublingual, vaginal, ocular and rectal) and inhalation routes. The vehicle can be administered to the patient in a variety of modes include parenterally, intravenously, intradermally, subcutaneously, intramuscularly, colonically, rectally or intraperitoneally methods.

The vehicle can be delivered systemically to a patient by several means. In one aspect of the invention, the drug containing vehicle can be introduced into a patient's blood vessel lumen, such as an artery or vein, via percutaneous injection via a syringe with a needle.

In another aspect of the invention, the vehicle can be delivered systemically to a patient through a needle catheter. This involves the needle catheter getting access to a blood vessel, followed by the introduction of a wire through the lumen of the needle. Through the wire access other catheters can be placed into the patient's blood vessel for extended treatments over a longer period of time. Alternatively, the vehicle can be delivered to a patient's blood vessel lumen by implantation of a medical implant such as a filter or a stent into the blood vessel.

The claim compositions are formulations for different delivery methods described herein. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995), Hoover, John E., Remington's Pharmaceutical Sciences, Mack Publishing Co., Easton, Pa. 1975, Liberman, H. A. and Lachman, L., Eds., Pharmaceutical Dosage Forms, Marcel Decker, New York, N.Y., 1980, and Pharmaceutical Dosage Forms and Drug Delivery Systems, Seventh Ed. (Lippincott Williams & Wilkins 1999).

C. Methods of Treatment

Pharmaceutical agents such as peptide and protein, antibody, vaccine and gene based drugs, in general may not be delivered using these routes because they might be susceptible to enzymatic degradation or cannot be absorbed into the systemic circulation efficiently due to molecular size and charge issues to be therapeutically effective. The invention provides for a method of treating a patient in need of therapeutic delivered by the claimed targeted drug delivery vehicle. It is envisioned that the method of treatment for a disease using the drug delivery vehicle to administer peptide/protein or peptide mimetic, antibody, vaccine and gene based drugs pharmaceuticals to a patient in need of prophylactic or therapeutic treatment.

Examples of drugs to be used in the method of treatment of a patient in need of therapeutic treatment include, but are not limited to, low-molecular inorganic compounds, low-molecular organic compounds, polymeric inorganic compounds, polymeric organic compounds, peptides, and nucleic acids. Examples of peptides that can be administered to a patient using the drug delivery vehicle include a peptide having biological molecule activation or inhibitory action. Examples of nucleic acids encoding peptides or nucleic acids that can be administered to a patient using the drug delivery vehicle include a nucleic acid encoding a peptide having biological molecule activation or inhibitory action. In addition, a peptide or a nucleic acid capable of controlling transcription or translation of biological molecules and a nucleic acid encoding such peptide or nucleic acid can be administered to a patient using the drug delivery vehicle.

In one application, the invention provides for a method of treating a patient with the drug delivery vehicle carrying a monocolonal antibody therapeutic. Examples of diseases to be treated by the claimed method include, but are not limited to, abciximab for cardiovascular disease, adalimumab for auto-immune disorders, alemtuzumab for chronic lymphocytic leukemia, basiliximab for transplant rejection, belimumab for systemic lupus erythematosus, bevacizumab for colorectal cancer and age related macular degeneration, brentuximab vedotin for anaplastic large cell lymphoma (alcl) and hodgkin lymphoma, canakinumab for treatment of cryopyrin-associated periodic syndromes (caps), cetuximab for colorectal cancer and head and neck cancer, certolizumab pegol for Crohn's disease, daclizumab for treatment of transplant rejection, denosumab for postmenopausal osteoporosis and solid tumor's bony metasteses, eculizumab for paroxysmal nocturnal hemoglobinuria, efalizumab for psoriasis, gemtuzumab for acute myelogenous leukemia (with calicheamicin), golimumab for rheumatoid arthritis, psoriatic arthritis, and ankylosing spondylitis, ibritumomab tiuxetan for non-hodgkin lymphoma, infliximab for autoimmune disorders, ipilimumab (mdx-101) for melanoma, muromonab-cd3 for transplant rejection, natalizumab for multiple sclerosis and Crohn's disease, atumumab for chronic lymphocytic leukemia, omalizumab for treatment of allergy-related asthma, palivizumab for respiratory syncytial virus, panitumumab for colorectal cancer, ranibizumab for macular degeneration, rituximab for non-hodgkin lymphoma, tocilizumab (or atlizumab) for rheumatoid arthritis, tositumomab for non-hodgkin lymphoma, and trastuzumab for breast cancer. In one application of the invention the drug delivery vehicle are used to administer monoclonal therapy to a patient. In another application of the drug delivery vehicle is administered to a patient as an admixture of the monoclonal therapy and an additional pharmaceutical agent and/or alternative therapeutic procedure.

The invention provides for a method of treating a patient in need of vaccination of a disease with a drug delivery carrying a therapeutic-effective amount of a vaccine. Examples of vaccines envisioned to be administrating using the drug delivery vehicle include, but are not limited to, anthrax vaccination by administering AVA (BioThrax) and equivalents thereof, chickenpox (varicella) vaccination by administering VAR (Varivax), MMRV (ProQuad) and equivalents thereof, diphtheria vaccination by administering DTaP (Daptacel, Infanrix), Td (Decavac, generic), DT (-generic-), Tdap (Boostrix, Adacel), DTaP-IPV (Kinrix), DTaP-HepB-IPV (Pediarix), DTaP-IPV/Hib (Pentacel) and DTaP/Hib and equivalents of, hepatitis A vaccination by administering HepA (Havrix, Vaqta), HepA-HepB (Twinrix) and the alike, hepatitis B vaccination by administering HepB (Engerix-B, Recombivax HB), Hib-HepB (Comvax), DTaP-HepB-IPV (Pediarix), HepA-HepB (Twinrix) and equivalents thereof, HIB vaccination by administering Hib (ActHIB, PedvaxHIB, Hiberix), Hib-HepB (Comvax), DTaP/Hib, DTaP-IPV/Hib (Pentacel), and equivalents thereof, HPV vaccination by administering HPV4 (Gardasil), HPV2 (Cervarix) and equivalents thereof, influenza (seasonal flu) vaccination by administering TIV (Afluria, Agriflu, FluLaval, Fluarix, Fluvirin, Fluzone, Fluzone High-Dose, Fluzone Intradermal), LAIV (FluMist) and equivalents thereof, measles vaccination by administering MR (M-M-R II), MMRV (ProQuad) and equivalents thereof, meningococcal vaccination by administering Polio (Ipol), DTaP-IPV (Kinrix), DTaP-HepB-IPV (Pediarix), DTaP-IPV/Hib (Pentacel) and equivalents thereof, rabies vaccination by administering Rabies (Imovax Rabies, RabAvert) and equivalents thereof, rotavirus vaccination by administering RV1 (Rotarix), RV5 (RotaTeq) and equivalents, rubella vaccination by administering MMR (M-M-R II), MMRV (ProQuad) and equivalents thereof, shingles (herpes zoster) vaccination by administering ZOS (Zostavax) and equivalents thereof, smallpox vaccination by administering Vaccinia (ACAM2000) and equivalents, tetanus vaccination by administering DTaP (Daptacel, Infanrix), Td (Decavac, generic), DT (-generic-), TT (-generic-), Tdap (Boostrix, Adacel), DTaP-IPV (Kinrix), DTaP-HepB-IPV (Pediarix), DTaP-IPV/Hib (Pentacel), DTaP/Hib and equivalents thereof, tuberculosis vaccination by administering BCG (TICE BCG, Mycobax) and the alike, typhoid vaccination by administering Typhoid Oral (Vivotif), Typhoid Polysaccharide (Typhim Vi) and equivalents thereof, yellow fever vaccination by administering YF (YF-Vax). Any such therapeutic agents can be used in conjunction with the drug vehicle delivery system to a patient in need of vaccination.

In one application of the invention method of treating a patient suffering from hyperproliferative disorder with a claimed targeted drug delivery vehicle associated with a therapeutic-effective dose of a chemotherapeutic. Non-limiting examples of hyperproliferative disorders envisioned to be treated using the method include, benign, pre-malignant, or malignant tumors and cancerous diseases such as carcinomas, gliomas, mesotheliomas, melanomas, lymphomas, leukemias, adenocarcinomas, rhabdomyosarcoma, primary thrombocytosis, primary macroglobulinemia, small-cell lung tumors, non-small-cell lung tumors, primary brain tumors, stomach cancer, renal cancer, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, cervical cancer, endometrial cancer, adrenal cortical cancer, myeloid leukemia, small tissue sarcomas, osteosarcomas, Burkitt's lymphoma, head and neck cancer, colon cancer, colorectal cancer, cancer of the esophagus, pancreatic cancer, skin cancers, hepatobiliary cancer, cancer of the gallbladder, cancer of the small intestine, rectal cancer, kidney cancer, bladder cancer, brain cancer, blood cancers, prostate cancer, penile cancer, urethral cancer, testicular cancer, vaginal cancer, uterine cancer, ovarian cancer, parathyroid cancer, adrenal cancer, pancreatic endocrine cancer, carcinoid cancer, bone cancer, retinoblastomas, multiple myelomas, Hodgkin's lymphoma, and non-Hodgkin's lymphoma.

Chemotherapeutic drugs envisioned to be administered by the drug delivery vehicle to a patient suffering from a hyperproliferative disease include, but are not limited to, alkylating agents, antimetabolites, anthracyclines, alkaloids, topoisomerase inhibitors, and other antitumour agents.

Alkylating agents act by chemically modifying a cell's DNA causing DNA damage in the cell. Specifically, the act by attaching an alkyl group to the guanine base of DNA, at the number 7 nitrogen atom of the purine ring. Some examples of alkylating agents include, but are not limited to, nitrogen mustards which include cyclophosphamide, mechlorethamine, uramustine or uracil mustard, melphalan, chlorambucil, ifosfamide. Some examples of alkylating agents include, but are not limited to, nitrosoureas which include carmustine, lomustin and streptozocin. Some examples of alkylating agents include, but are not limited to, alkyl sulfonates which include busulfan. In one application, the invention provides for a method of treating a cancer patient with the drug delivery vehicle carrying a therapeutic effective amount of an alkylating agent therapeutic.

Platinum-based chemotherapeutic drugs act in a similar manner as alkylating agents and as a result are sometimes described as "alkylating-like". These agents do not have an alkyl group, but nevertheless damage DNA by permanently coordinate to DNA, and in turn interfere with the cells ability to perform DNA repair. Some examples include, but are not limited to, cisplatin, carboplatin, nedaplatin, oxaliplatin, satraplatin and triplatin tetranitrate. In one application, the invention provides for a method of treating a cancer patient with the drug delivery vehicle carrying a therapeutic effective amount of a platinum-based therapeutic.

Anti-metabolites are chemicals that inhibit the use of a metabolite in its normal biological process. Anti-metabolites often have similar structure to the metabolite that they interfere with. For example, anti-metabolites can impersonate nucleotide bases such as purines or pyrimidine and as a result become inserted as a "nucleotide bases" of the DNA. Their insertion into the DNA ultimately prevents normal cellular development and division. In addition, anti-metabolites can also negatively affect RNA synthesis. Examples of anti-metabolites include, but are not limited to, azathioprine and mercaptopurine. Owing to their efficiency at halting cell growth and cell division anti-metabolites drugs are one of the most widely used cytostatics. In one application, the invention provides for a method of treating a cancer patient with the drug delivery vehicle carrying a therapeutic-effective amount of an anti-metabolite.

Alkaloids are a group of naturally occurring chemical compounds that contain mostly basic nitrogen atoms. Alkaloids are produced by a large variety of organisms and are part of the group of secondary metabolites. While alkaloids have many pharmacological affects, some alkaloids can have anti-cancer properties primarily by blocking cell division. Anti-cancer alkaloids such as vinca alkaloids and taxanes block cell division by preventing microtubule function. Vinca alkaloids block cell division, by binding to specific sites on tubulin, inhibiting the assembly of tubulin into microtubules (M phase of the cell cycle). Examples of vinca alkaloids include, but are not limited to, vincristine, vinblastine, vinorelbine, and vindesine. Taxanes block cell division by enhancing the stability of microtubules which, in turn, prevents the separation of chromosomes during anaphase of the cell cycle. Some examples of taxanes include, but are not limited to, taxol and docetaxel. In one application, the invention provides for a method of treating a cancer patient with the drug delivery vehicle carrying a therapeutic-effective amount of an alkaloid.

Topoisomerases are essential enzymes that maintain the topology of DNA. Topoisomerase inhibitors to type I or type II topoisomerases interferes with both transcription and replication of DNA by disrupting the proper supercoiling formation of DNA. Some examples of type I topoisomerase inhibitors include, but are not limited to, camptothecins, irinotecan and topotecan. Some examples of type II topoisomerase inhibitors, include but are not limited, to amsacrine, etoposide, etoposide phosphate, and teniposide. In one application, the invention provides for a method of treating a cancer patient with the drug delivery vehicle carrying a therapeutic effective amount of an topoisomerases therapeutic.

Other antitumor agents include monoclonal antibodies and kinase inhibitors and cytotoxic antibiotics. Some examples of cytotoxic antibiotics include, but are not limited, actinomycin, bleomycin, plicamycin, and mitomycin. Other cytotoxic antibiotics include anthracyclines, such as doxorubicin, daunorubicin, valrubicin, idarubicin, and epirubicin. In one application, the invention provides for a method of treating a patient with the drug delivery vehicle carrying a therapeutic effective amount of a cytotoxic antibiotic therapeutic.

Other chemotherapeutic drugs envisioned to be administered by the claimed drug delivery vehicle suffering from a hyperproliferative disease or cancer include, but are not limited to, 13-cis-Retinoic Acid, 2-CdA, 2-Chlorodeoxyadenosine, 5-Azacitidine, 5-Fluorouracil 5-FU, 6-Mercaptopurine, 6-MP, 6-TG, 6-Thioguanine, Abraxane, Accutane® (Isotretinoin), Actinomycin-D, Adriamycin® (Doxorubicin), Adrucil® (5-fluorouracil and 5-FU), Afinitor® (Everolimus), Agrylin®, Ala-Cort®, Aldesleukin, Alemtuzumab, ALIMTA, Alitretinoin, Alkaban-AQ®, Alkeran®, All-transretinoic acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Axitinib, Azacitidine, BCG, BCNU, Bendamustine, Bevacizumab, Bexarotene, BEXXAR®, Bicalutamide, BiCNU, Blenoxane® Bleomycin, Bortezomib, Busulfan, Busulfex®, C225, Cabazitaxel, Calcium Leucovorin, Campath® Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate, Dexasone, Dexrazoxane, DHAD, DIC, Diodex Docetaxel, Doxil®, Doxorubicin, Doxorubicin Liposomal, Droxia™, DTIC, DTIC-Dome®, Duralone, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Inlyta®, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Jevtana®, Kidrolase(t), Lanacort®, Lapatinib, L-asparaginase, LCR, Lenalidomide Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin® (vincristine), Ontak® (Denileukin diftitox), Onxa™ (Paclitaxel), Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRONT™, PEG-L-asparaginase, PEM-ETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine, Implant, Provenge®, Purinethol®, Raloxifene, Revlimid®, Rheumatrex®, Rituxan®, Rituximab, Roferon-A® (Interferon Alfa-2a), Romiplostim, Rubex® (doxorubicin), Rubidomycin hydrochloride, Sandostatin®, Sandostatin LAR®, Sargramostim, Sipuleucel-T, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza or Zometa®.

The term "diabetes mellitus" refers to a group of diseases that affect how the body uses blood glucose. Chronic diabetes conditions include type 1 diabetes and type 2 diabetes. Depending on what type of diabetes patient has insulin may play a role in treatment. Many types of insulin are available, including rapid-acting insulin, long-acting insulin and intermediate options. A patient may be prescribing one of theses or a mixture of insulin types. Examples of insulin or insulin analog products include, but not limited to, Humulin®, Humalog®, Lantus®., Novolog®, Mix70/30 and Humalog is a human insulin analog that is a rapid-acting, parenteral blood glucose-lowering agent. Humulin L is an amorphous and crystalline suspension of human insulin with a slower onset and a longer duration of activity compared to regular insulin. Humulin U is a crystalline suspension of human insulin with zinc providing a slower onset and a longer and less intense duration of activity compared to regular insulin or the intermediate-acting insulins (NPH and Lente).

Other medications used for treatment of diabetes, function to stimulate your pancreas to produce and release more insulin. Another type of medication that can be prescribed for diabetes are pharmaceutical agents that inhibit the production and release of glucose from your liver. Another type of medication can be prescribed are drugs that block the action of stomach enzymes that break down carbohydrates or make your tissues more sensitive to insulin. In another aspect of the invention, provides for a method of treating a subject with diabetes mellitus with a targeted drug delivery vehicle associated with a therapeutic-effective amount of insulin or insulin analog or other diabetes mellitus pharmaceutical agents.

Cholesterol-containing deposits (plaques) on the walls of arteries are generally the cause of most coronary artery disease cases. As plaques build up on the walls, they narrow the flow space of the coronary arteries, resulting in the heart to receive less blood than without the plaques. A complete blockage of flow to the coronary artery can cause a heart attack. Statins or HMG-CoA reductase inhibitors are commonly used for the treatment of coronary artery disease or to lower cholesterol levels in people at risk for cardiovascular disease owing to hypercholesterolemia.

Statins act by competitively inhibiting HMG-CoA reductase, an enzyme of the HMG-CoA reductase pathway, the metabolic pathway for cholesterol synthesis. Although the statins' function is to inhibit endogenous cholesterol synthesis, their actions goes further than that. By reducing intracellular cholesterol levels, they cause liver cells to upregulate expression of the LDL receptor, leading to increased clearance of low-density lipoprotein from the bloodstream. Statins also exhibit additional mechanisms beyond lipid-lowering activity in the prevention of atherosclerosis via four proposed mechanisms: improving endothelial function, modulating inflammatory responses, maintaining plaque stability, and preventing thrombus formation. An example of the statins include, but are not limited to, atorvastatin, cerivastatin, fluvastatin, lovastatin, mevastatin, pravastatin, pravachol, selektine, lipostat, rosuvastatin (crestor), simvastatin, zocor, lipex and pitavastatin. Statin therapy has been shown to significantly reduce morbidity and mortality in diabetic patients. In one aspect of the invention, the invention provides for a method of treating a subject with coronary artery disease using the claimed vehicle associated with a therapeutic-effective of statin. In another aspect, the invention provides for a method of treating a subject with coronary artery disease using the claimed vehicle associated with a therapeutic-effective amount of insulin. In another aspect of the invention, the invention provides for a method of treating a subject with coronary artery disease using vehicle co-encapsulating therapeutic-effective amount of both insulin and statin.

In practicing the method of treatment of the present invention, the drug delivery vehicle can be used alone or in combination with other therapeutics, surgical or diagnostic approaches. The other therapeutic approaches or agents can be administered at the same time as the drug delivery vehicle associated with drugs, separately or at different times.

Combination drug therapies can also be employed with drug delivery vehicle. They can be administered separately or together by the same drug delivery vehicle containing one or more of the drugs, such as an admixture, such that that they can administered coincidentally into the cell. Where one or more drugs are administered in separate drug delivery vehicles, the timing and schedule of administration of each drug can vary.

Owing to the small size of the claimed drug delivery vehicle, it is predicted to be able to cross the blood-brain barrier. The invention provides for a method of treatment for diseases that affect the brain tissue, for examples, brain tumors, Alzheimer's disease, Parkinson's disease, dementia, Huntington's disease, Creutzfeldt-Jakob (Mad Cow) disease and stroke patients.

A brain tumor is a mass or growth of abnormal cells in your brain. Some brain tumors are noncancerous (benign), and some brain tumors are cancerous (malignant). Brain tumors can begin in your brain (primary brain tumors), or cancer can begin in other parts of your body and spread to your brain (secondary, or metastatic, brain tumors). Brain tumor treatment options depend on the type of brain tumor you have, as well as its size and location. Invention provides a method for treatment for brain cancer using the claimed vehicle associated with a therapeutic effective amount of an anti-cancer agent, for example the chemotherapeutic described herein and in combination with other treatments such as gamma knife and surgical treatments.

Alzheimer's disease (AD) the most common form of dementia. In general, pathological effects of AD present in a person patient over 65 years of age. The cause and progression of AD are not well understood. Two types of drugs are currently used to treat cognitive symptoms associated with AD include, cholinesterase inhibitors and Memantine. These drugs work by boosting levels of a cell-to-cell communication. Examples of cholinesterase inhibitors include, but are not limited to, donepezil (Aricept), galantamine (Razadyne) and rivastigmine (Exelon). Memantine (Namenda) can be administered alone or sometimes used in combination with a cholinesterase inhibitor. In one aspect of the invention cholinesterase inhibitors or Memantine is associated with the targeted drug vehicle and administrated to patient diagnosed with AD. In another aspect of the invention cholinesterase inhibitors or Memantine is association or co-associated with targeted drug vehicle as an admixture and administrated to patient diagnosed with AD.

Parkinson's disease (PD) is a progressive disorder of the nervous system that affects your movement. The presence of Lewy bodies clumps of specific substances, including a-synuclein within brain cells are markers of a patient affected by Parkinson's disease. Both medications and Surgical procedures are use to help control can help control symptoms of Parkinson's disease. Example of medications given to PD patient can include but are not limited to, Carbidopa-levodopa (Parcopa), Dopamine, Dopamine agonists, MAO B inhibitors, Catechol O-methyltransferase (COMT) inhibitors, Anticholinergics, and Amantadine. In another aspect of the invention the drug targeted vehicle is associated with an anti-Parkinson's disease therapeutic agents and administrated to patient diagnosed with Parkinson's disease alone, in combination or as an admixture, for example, with any of the described therapeutic above or with surgical treatment.

Huntington's disease is an inherited disease that causes the progressive breakdown of nerve cells in the brain. Clinical symptoms usually manifest around the 40 to 50 years of age. The effect can result in inhibition of a patient's movement and cognitive functions and sometime can result in the development of psychiatric disorders. Medications for movement disorders include etrabenazine (Xenazine), Antipsychotic drugs, such as haloperidol (Haldol) and clozapine (Clozaril) Other medications such as clonazepam (Klonopin) and antianxiety drugs such as diazepam (Valium) may also be useful. Medications for psychiatric systems include antidepressants include such drugs as escitalopram (Lexapro), fluoxetine (Prozac, Sarafem) and sertraline (Zoloft). Antipsychotic drugs can help prevent the psychological highs and lows include lithium (Lithobid) and anticonvulsants, such as valproic acid (Depakene), divalproex (Depakote) and lamotrigine (Lamictal). In another aspect of the invention the targeting drug vehicle is associated with anti-Huntington's disease therapeutic agents and administrated to patient diagnosed with Huntington's disease alone, in combination or as an admixture with another therapeutic agent, for examples the one listed above.

Creutzfeldt-Jakob (Mad Cow) disease is a degenerative brain disorder that leads to dementia and, ultimately, death. Currently, no effective treatment exists for Creutzfeldt-Jakob disease or any of its variants. In another aspect of the invention the targeted drug vehicle is associated with one or more anti-Creutzfeldt-Jakob therapeutic agents and administrated to patient diagnosed with Creutzfeldt-Jakob disease.

D. Administration Frequency and Dosing

The claimed targeted dug delivery vehicle can be administered as frequently as necessary, including hourly, daily, weekly or monthly, as determined by the treating physician. Determination of the proper dosage for a particular situation is within the skill of the clinical practitioner. For example, dosages can be empirically determined by considering the diagnosis of the type and stage of disease, as determined by the treating physician. The dose administered to a patient, in the context of the present invention should be sufficient to affect a beneficial therapeutic response in the patient over time. However, the dosages and frequency of the pharmaceutical agent given to a particular patient will vary depending upon the requirements of the patient, the severity of the condition being treated, and the efficacy and toxicity pharmaceutical agent being given. For example, the compounds utilized method of treatment of the invention can be administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. It is envisioned with the application of the present invention that dosing can be significantly above or the normal dosing levels used with conventional drug delivery methods as discussed herein.

Daily dosing of the vehicle associated with a pharmaceutical agent may be divided and administered in portions during the day, as determined by the treating physician. Doses can be given daily, or on alternate days or alternatively they can also be given on a regular or continuous basis over longer periods of time e.g. weeks, months or years, as determined by the treating physician. Determination of the proper dosage for a particular situation is within the skill of the clinical practitioner. Generally, treatment is initiated with smaller dosages which are less than the optimum dose of the compound. Thereafter, the dosage is increased by small increments until the optimum effect under circumstances is reached, as determined by the treating physician.

In applying the methods of treatment using the claimed vehicle it is envisioned that the dosing using the drug can performed with very high doses, owing to reduced toxicity effects through targeting 20%, 30%, 40%, 50% 60%, 70%, or 80% of normal concentration given by conventional methods to yield a equivalent of better therapeutic effect on disease being treated. In another application of the method of treatment using the claimed vehicle it is envisioned that this application will allow for the lowering of the normal concentration given by conventional methods, owing to enhanced delivery of drug through targeting to 10%, 20%, 30% or 40% to yield a therapeutic effect on the disease being treated.

E. Combination Method of Treatments

In practicing the methods of the present invention, the vehicle associated with a pharmaceutical agent can be administrated alone, or it can be administrated in combination with other therapeutics. Other therapeutics for example can include, but are not limited to, therapeutic agents, surgical methods, radiation methods, diagnostic methods or agents.

Methods for experimentally determining therapeutically-effective dosages of the vehicle associated with a pharmaceutical drugs and other agents for use in combination treatment regimens include the use of i.e., by providing more frequent, lower doses in an effort to minimize any undesirable side-effects. Combination treatment regimens encompass administration of the drug containing vehicle described herein is initiated prior to, during, or after treatment with a second agent described above, and continues until any time during treatment with the second agent or after termination of treatment with the second agent. Furthermore, combination regimens also include treatments in which a vehicle encapsulated a second agent being used in combination are administered simultaneously or at different times and/or at decreasing or increasing intervals during the treatment period. Combination treatments further include periodic treatments that start and stop at various times to assist with the clinical management of the patient. For example, combination treatment with the vehicle can be is administered weekly at the onset of treatment, decreasing to biweekly, and decreasing further as appropriate Radiation can be given as a curative modality, either alone or in combination with surgery and/or chemotherapy. It may also be used to relieve symptoms in patients with incurable cancers. Radiation therapy works by damaging the DNA of cancerous cells causing them to halt proliferation or die. This DNA damage is caused by one of two types of energy, photon or charged particle. The most common form of radiation therapy is intensity-modulated radiation therapy (IMRT). IMRT relies on photons and the majority of the radiation effect is through free radicals. Another type of radiation used to charged particle therapy. This type of radiation uses charged particles such as proton, boron, carbon, and neon ions can cause direct damage to cancer cell DNA through high-LET (linear energy transfer and act mostly via direct energy transfer usually causing double-stranded DNA break to cause cell death of the cancer cell. The amount of radiation used in photon radiation therapy is measured in gray (Gy), and varies depending on the type and stage of cancer being treated. For curative cases, the typical dose for a solid epithelial tumor ranges from 60 to 80 Gy, while lymphomas are treated with 20 to 40 Gy. For example, combination treatments for the treatment of cancers provided but the invention include radiation from 20 to 40 Gy either in combination with surgery and/or chemotherapy delivered by the drug delivery particle.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

Example 1

Preparation of Drug Associated Vehicle with Sodium Cholate Dialysis

The amino acid chain (SEQ ID NO: 20) was synthesized by a solid-phase procedure, using a Fmoc/DIC/HOBt protocol on a Biosearch 9600 peptide synthesizer (Applied Biosystems, Foster City, Calif.). Both L-amino acid (L-37pA) and D-amino acid (D-37pA) enantiomers were synthesized. All peptides were purified to greater than 98% homogeneity by reverse-phase HPLC on an Aquapore RP-300 column. Then the Myristic acid was covalent attached to the amino acid chain.

1. Myristoyl-5A peptide (final conc.: 0.5 mg/ml) in 2 ml PBS and the drug (valrubicin) in DMSO are mixed by vortexing.
2. 14 mg sodium cholate is added and the volume is increased to 2 ml with buffer (10 mM Tris, 0.1M KCl, 1 mM EDTA pH 8.0).
3. The mixture is mixed thoroughly by vortexing and incubated overnight at 4° C.
4. The mixture is then dialyzed (MW cutoff 2000 kD dialysis bag) against 1 liter of PBS for 48 hours with at least 4 changes of buffer.
5. The recovered vehicle solution/suspension centrifuged at 5,000 RPM for 5 minutes and then filter sterilized by passing through 0.2 µM syringe filter.
6. Incorporation efficiency (vehicle content vs. original amount of drug used) is determined by using various methods depending on the type of drug used. (e.g. spectrophotometry, fluorometry, radioactivity etc.).

Example 2

Specificity of Targeting Drug Delivery Vehicle on Cancer Cells Vs Non-maligent Cells Culturing of the malignant non malignant cell lines were carried out according to procedures and culturing conditions provided by the ATCC. Briefly the cells were cultured in Roswell Park Memorial Institute 1640 (RPMI 1640) with 10% fetal bovine serum. A non malignant prostate epithelial cell line (PZ-HPV) was grown in keratinocyte medium supplemented with 10% fetal bovine serum medium containing human recombinant epidermal growth factor and bovine pituitary extract as per manufacture's instructions.

Example 3

Solubility Study in Target Drug Delivery Vehicle

The solubility of paclitaxel in a series of dissolution media containing different amount of sodium lauryl sulphate (SLS can be determined. The number of folds of saturation volume (FSV) provided by 900 ml of media for 2 mg paclitaxel can be estimated to assess the solubilising capacity of each media. The equilibrium solubility ($C_n$) of paclitaxel in phosphate buffer containing 0, 0.05, 0.25, 0.5, and 1.0% of SLS can be be 2.11.+−.0.01 ug/ml (FSV 0.9), 2.33.+−.0.15 ug/ml (FSV 1.0), 3.20.+−.0.16 ug/ml (FSV 1.4), 8.00.+−.0.39 ug/ml (FSV 3.6), and 119.+−0.29 ug/ml (FSV 53.6), respectively. According to the USP guideline, sink conditions can be achieved if drug concentrations are maintained at or below one-third of the saturation solubility. The solubility of paclitaxel can be increased in a non-proportional fashion with the addition of SLS. A minimum level of 0.5% SLS can be sufficient to provide sink conditions for paclitaxel dissolution (FSV>3). The dissolution pattern of pure paclitaxel and the various paclitaxel formulations can be studied using both sink (0.5% SLS) and non-sink (0% and 0.05% SLS) conditions. The experiment can be repeated for paclitaxel in a drug delivery vehicle of the present invention.

Example 4

In Vitro Dissolution Studies

An in vitro dissolution study can be performed in 900 ml of phosphate buffer (0.05 M, pH 7.2) containing 0, 0.05, and 0.5% (w/v) SLS, using USP 23 type II apparatus (paddle method) operating at 75.+−.0.02 rpm. Each sample, containing about 2 mg of celecoxib (equivalent to the amount used in the in vivo studies), can be added into the dissolution medium maintained at 37.+−.0.5.degree. C. Aliquots of 3 ml can be drawn at fixed time points and replaced with an equal volume of fresh dissolution medium. The drawn samples can be centrifuged at 9,400 g for 15 min to remove undissolved materials. The supernatant can be subjected to another cycle of centrifugation under the same conditions. An aliquot of 100 ul can be taken from the middle portion of each centrifuged samples before diluted 2-fold with acetonitrile. Centrifugation can be selected for phase separation of the samples because preliminary experimentscan show that most (Millipore) filters absorb celecoxib, therefore separation by filtration might not be employed. The amount of celecoxib dissolved in the dissolution media can be analysed by HPLC. The experiment can be repeated for celecoxib in a drug delivery vehicle of the present invention.

Example 5

In Vivo Pharmacokinetics Comparing Conventional Vs Target Drug Delivery Vehicle~Plasma Concentration Curves Each group can contained 5 mice). Each animal can be implanted subcutaneously with MDA-MB-435 breast cancer cells. When tumor grows to approximately 125 mm3 (100-150 mm3), animals can be pair-matched by tumor size into vehicle drug treatment group and control group free drug treatment group. One group can be dosed intravenously with (30 mg/kg paclitaxel) using conventional delivery and the other group can be dosed with the vehicle delivery/PTX (80 mg/kg paclitaxel). Blood samples (0.2 mL) can be collected from the jugular vein at designated time intervals and the cannula can be flushed with an equal volume of heparinised normal saline (50 units/5 ml) to prevent blood clotting. The collected blood samples can be centrifuged at 9,400 g for 5 min. An aliquot of 100 ul plasma can be vortex-mixed with 100 ul acetonitrile and centrifuged at 3,500 g for 10 min to remove proteins, prior to HPLC analysis. The recoveries of paclitaxel in the plasma can be determined.

Example 6

Therapeutic Index Drug Delivery Vehicle with Conventional Drug Delivery

By treating patients using the targeting vehicle composition, the therapeutic index of most, if not all, therapeutic agents can be increased.

Example 7

Competition of Targeting Drug Vehicle and HDL for the HDL Receptor

Drug delivery vehicles were prepared with the myristoylated (SEQ ID NO:20). These data show that human HDL suppresses the uptake of a drug carried by the drug delivery vehicles suggesting that the uptake of the drug is facilitated by the SR-B1 (HDL) receptor. Cells were plated in 24 well plates (100,000 cells/well) in their respective media. On the following day, the monolayers were washed with PBS, pH 7.4, and then incubated at 37° C. with serum free medium for 90 minutes. Cells were washed with PBS and incubated with a single concentration of the rHDL/AD-32 complex plus increasing amounts of HDL (0-120 μg) in serum free medium for 90 minutes. So that the uptake measurement will not include rHDL at the cell surface, the preparation was washed once with 1× PBS, pH 3.0 & then with 1× PBS, pH 7.4. The cells are then lysed with lysis buffer (50 mm Tris-HCl (pH 8.0), 150 mM NaCl, 0.02% Sodium Azide, 100 μg/ml PMSF, 1 μg/ml aprotinin and 1% Triton X-100). The lysate was centrifuged at 10,000 rpm for 5 minutes. The protein and AD-32 content of the lysate was determined by BCA assays and spectrophotometric/fluorometric measurements were carried out at 450 nm (absorbance) and excitation at 485 nm-emission at 525 nm (for fluorescence).

Example 8

Evaluation and Characterization of Reconstituted High Density Lipoprotein Nanoparticles Assembled with Apo A-I Mimetic Peptides 1. Design and Synthesis of Apo A-I Mimetic Peptides Four apo a-I mimetic peptides were synthesized, such that each peptide has an amphipathic helical configuration, and an affinity for the SR-B1 receptor. The sequences of the apo a-I mimetic peptides are shown below.

| NAME | CODE # | AMINO ACID SEQUENCE |
|---|---|---|
| Hydrophobic ELK-18M | 37878 | EKLLELLKKLLELLKELL (SEQ ID NO: 63) |
| Positively charged ELK-18M | 37877 | EKLKALLEKLLAKLKELL (SEQ ID NO: 64) |
| Neutral ELK-18M | 37874 | EKLKELLEKLLEKLKELL (SEQ ID NO: 65) |
| Negatively charged ELK-18M | 37875 | EELKEKLEELKEKLEEKL (SEQ ID NO: 66) |
| MYR-5A (control) | 30722 | |

2. Paclitaxel Encapsulation Efficiency into Myristoyl Peptide Nanoparticles Based on Measurements of $^3$H-paclitaxel Paclitaxel encapsulation efficiency into myristoyl peptide nanoparticles based on measurements of 3H-paclitaxel is shown in FIG. 8. Some turbidity was observed in all of the tested preparations. In order to clarify the preparations, the samples were centrifuged at 5,000 RPM for 5 minutes. This treatment resulted in substantial losses of radioactivity, indicating that most of the drug was loosely bound by the peptide complexes. However, the peptide 39877, retained 60% of the initial amount of paclitaxel, an efficiency level which is higher than experienced with the (control) MYR-5A peptide.

The use of a highly ionized detergent in the place of cholate may improve incorporation of paclitaxel. Removal of residual amounts of highly ionized detergents could be accomplished using ion exchange resins, if needed. While the incorporation of each drug may vary substantially with the chemical configuration of the (drug) starting material, each drug could be tested with each of the 4 model peptides to optimize incorporation.

3. mRNA Encapsulation Using MYR Conjugated Apo A-I Mimetic Peptides

In an embodiment of the present invention, ~2 kb mRNA was encapsulated to improve its functionality and bioavailability. mRNA was combined with phospholipid in the presence of detergent and particles of approximately 3 μm diameter were obtained. Upon addition of the MYR-5A peptide, a dramatic reduction in particle size was observed to ~500 nm. The smaller particle is suitable for efficient delivery of the mRNA to target cells and for therapeutic applications.

The invention claimed is:

1. A targeted drug delivery vehicle composition consisting essentially of: a drug composition and 5-50 targeted poly-amino-acid subunits,
   wherein each of the targeted poly-amino-acid subunits comprise a targeting amino acid chain conjugated to a fatty acid, and
   wherein the targeting amino acid chain comprises at least 70% identity to SEQ ID NOs: 20, 63, 64, 65, or 66; and has affinity to a scavenger receptor class B 1 or portion thereof.

2. The composition of claim 1, wherein the fatty acid is a saturated fatty acid.

3. The composition of claim 1, wherein the fatty acid is between 3 and 15 carbons in length.

4. The composition of claim 1, wherein the fatty acid is myristic acid.

5. The composition of claim 1, wherein the targeting amino acid chain and the fatty acid are in a ratio of 1:1.

6. The composition of claim 1, wherein the targeting amino acid chain is covalently linked to the fatty acid.

7. The composition of claim 1, wherein the targeting amino acid chain comprises one or more amphipathic alpha-helical domains.

8. The composition of claim 7, wherein the targeting amino acid chain comprises two amphipathic alpha-helical domains.

9. The composition of claim 1, wherein the targeted poly-amino-acid subunits further comprise a targeting amino acid sequence that has affinity to a transmembrane molecule.

10. The composition of claim 1, wherein the targeted poly-amino-acid subunits further comprise a targeting amino acid sequence that has affinity to a receptor.

11. The composition of claim 1, wherein the targeted poly-amino-acid subunits further comprise a targeting amino acid sequence that has affinity to HDL receptor.

12. The composition of claim 1, wherein the targeted poly-amino-acid subunits further comprise a targeting amino acid sequence that has affinity to rapidly dividing cells.

13. The composition of claim 1, wherein the targeted poly-amino-acid subunits further comprise a targeting amino acid sequence that has affinity to cancer cells.

14. The composition of claim 1, wherein the targeted drug delivery vehicle does not comprise an unesterified cholesterol, a cholesteryl ester, a phospholipid, a phosphatidylcholine, a phosphatidylserine, a phosphatidylethanolamine, a phosphatidylinositol, or a sphingomyelin.

15. The composition of claim 1, wherein the targeted poly-amino-acid subunits further comprise one or more compounds selected from the group consisting of: an unesterified cholesterol, a palmitoyl-oleoyl phosphatidylcholine, a phospholipid, an apolipoprotein A-1 protein, and an amino acid chain comprising at least 70% identity to SEQ ID NOs: 20, 63, 64, 65, or 66.

16. The composition of claim 1, wherein the targeted drug delivery vehicle has a diameter of about 20 nm to 300 nm.

17. The composition of claim 1, wherein the drug composition comprises a hydrophobic drug, cytotoxic drug, antibody drug, protein or peptide drug, mimetic peptide drug, nucleic acid drug, a vaccine drug or any combination or salt thereof.

18. The composition of claim 1, wherein the drug composition comprises an albumin or a nonionic surfactant.

19. The composition of claim 18, wherein the nonionic surfactant is a polyoxyl castor oil.

20. A targeted drug delivery vehicle consisting essentially of: a drug composition and 5-50 targeted poly amino-acid subunits,
   wherein each of the targeted poly-amino-acid subunits comprise a polynucleotide drug composition, a phospholipid, an excipient, and a targeting amino acid chain, and
   wherein the targeting amino acid chain comprises at least 70% identity to SEQ ID NOs: 20, 63, 64, 65, or 66, and has affinity to a scavenger receptor class B 1 or a portion thereof.

21. The targeted drug delivery vehicle of claim 20, wherein the phospholipid is phosphatidylcholine.

22. The targeted drug delivery vehicle of claim 20, wherein the targeted drug delivery vehicle has a diameter of about 300 nm to 1000 nm.

23. The targeted drug delivery vehicle of claim 20, wherein the polynucleotide drug composition is neutralized before incorporation into the targeted drug delivery vehicle.

24. The composition of claim 1, wherein the targeted drug delivery vehicle does not comprise an apolipoprotein A-1 protein.

25. The composition of claim 1, wherein the scavenger receptor class B 1 functions as a HDL receptor.

26. The composition of claim 1, wherein the scavenger receptor class B 1 functions as a LDL receptor.

27. The composition of claim 1 or claim 20, wherein the affinity to the scavenger receptor class B 1 or a portion thereof promotes uptake of the drug composition into a target cell.

28. The composition of claim 1 or claim 20, wherein the targeting amino acid chain is about 10 to 40 amino acids in length.

29. Previously Presented) The composition of claim 1 or claim 20, wherein the targeting amino acid chain is SEQ ID NO: 20, 63, 64, 65, or 66.

30. A targeted drug delivery vehicle composition consisting essentially of:
   a drug composition and 5-50 targeted poly-amino-acid subunits,
   wherein each of the targeted poly-amino-acid subunits comprise a targeting amino acid chain conjugated to a fatty acid, and
   wherein the targeting amino acid chain: (a) comprises at least 70% identity to SEQ ID NOs: 20, 63, 64, 65, or 66; (b) forms one or more amphipathic alpha-helical domains; and (c) has affinity to a scavenger receptor class B 1 or a portion thereof.

31. A targeted drug delivery vehicle composition consisting essentially of: a drug composition and 5-50 targeted poly-amino-acid subunits,
   wherein each of the targeted poly-amino-acid subunits comprise a targeting amino acid chain conjugated to a fatty acid, and
   wherein the targeting amino acid chain: (a) comprises at least 70% identity to SEQ ID NOs: 20, 63, 64, 65, or 66; (b) forms one or more amphipathic alpha-helical domains; (c) has affinity to a scavenger receptor class B 1 or a portion thereof; and (d) promotes uptake of the drug composition into a target cell.

* * * * *

SEQUENCE LISTING

```
<160> NUMBER OF SEQ ID NOS: 66

<210> SEQ ID NO 1
<211> LENGTH: 4
<212> TYPE: PRT
<213> ORGANISM: Artificial Sequence
<220> FEATURE:
<223> OTHER INFORMATION: Synthesized

<400> SEQUENCE: 1

Arg Lys Asn Arg
1

<210> SEQ ID NO 2
<211> LENGTH: 5
<212> TYPE: PRT
<213> ORGANISM: Artificial Sequence
<220> FEATURE:
<223> OTHER INFORMATION: Synthesized

<400> SEQUENCE: 2

Lys Lys Trp Val Arg
1               5

<210> SEQ ID NO 3
<211> LENGTH: 3
<212> TYPE: PRT
<213> ORGANISM: Artificial Sequence
<220> FEATURE:
<223> OTHER INFORMATION: Synthesized

<400> SEQUENCE: 3

Arg Gly Asp
1

<210> SEQ ID NO 4
<211> LENGTH: 9
<212> TYPE: PRT
<213> ORGANISM: Artificial Sequence
<220> FEATURE:
<223> OTHER INFORMATION: Synthesized

<400> SEQUENCE: 4

Asp Val Glu Trp Val Asp Val Ser Tyr
1               5

<210> SEQ ID NO 5
<211> LENGTH: 12
<212> TYPE: PRT
<213> ORGANISM: Artificial Sequence
<220> FEATURE:
<223> OTHER INFORMATION: Synthesized

<400> SEQUENCE: 5

Arg Lys Lys Arg Arg Gln Arg Arg Arg Pro Pro Gln
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthesized

<400> SEQUENCE: 6
```

```
Arg Arg Arg Gln Arg Arg Lys Lys Arg
1               5

<210> SEQ ID NO 7
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (4)..(4)
<223> OTHER INFORMATION: Xaa can be any naturally occurring amino acid

<400> SEQUENCE: 7

Arg Arg Pro Xaa Arg
1               5

<210> SEQ ID NO 8
<211> LENGTH: 16
<212> TYPE: PRT
<213> ORGANISM: Artificial Sequence
<220> FEATURE:
<223> OTHER INFORMATION: Synthesized

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 30
<212> TYPE: PRT
<213> ORGANISM: Artificial Sequence
<220> FEATURE:
<223> OTHER INFORMATION: Synthesized

<400> SEQUENCE: 9

Gly His Glu Asp Thr Met Ala Asp Gln Glu Ala Asn Arg His Gly Arg
1               5                   10                  15

Ser Gly Gly Asp Pro Asn Tyr Tyr Arg Pro Pro Gly Gly Tyr
            20                  25                  30

<210> SEQ ID NO 10
<211> LENGTH: 20
<212> TYPE: PRT
<213> ORGANISM: Artificial Sequence
<220> FEATURE:
<223> OTHER INFORMATION: Synthesized

<400> SEQUENCE: 10

Gly Phe Phe Ser Phe Ile Gly Glu Ala Phe Gln Gly Ala Gly Asp Met
1               5                   10                  15

Trp Arg Ala Tyr
            20

<210> SEQ ID NO 11
<211> LENGTH: 11
<212> TYPE: PRT
<213> ORGANISM: Artificial Sequence
<220> FEATURE:
<223> OTHER INFORMATION: Synthesized

<400> SEQUENCE: 11

Lys Ala Glu Tyr Lys Lys Asn Lys His Arg His
1               5                   10
```

<210> SEQ ID NO 12
<211> LENGTH: 11
<212> TYPE: PRT
<213> ORGANISM: Artificial Sequence
<220> FEATURE:
<223> OTHER INFORMATION: Synthesized

<400> SEQUENCE: 12

Tyr Thr Arg Leu Thr Arg Lys Arg Gly Leu Lys
1               5                   10

<210> SEQ ID NO 13
<211> LENGTH: 18
<212> TYPE: PRT
<213> ORGANISM: Artificial Sequence
<220> FEATURE:
<223> OTHER INFORMATION: Synthesized

<400> SEQUENCE: 13

Asp Trp Leu Lys Ala Phe Tyr Cys Lys Val Ala Glu Lys Leu Lys Glu
1               5                   10                  15

Ala Phe

<210> SEQ ID NO 14
<211> LENGTH: 18
<212> TYPE: PRT
<213> ORGANISM: Artificial Sequence
<220> FEATURE:
<223> OTHER INFORMATION: Synethsized

<400> SEQUENCE: 14

Asp Trp Leu Lys Ala Phe Tyr Asp Lys Val Ala Glu Lys Leu Lys Cys
1               5                   10                  15

Ala Phe

<210> SEQ ID NO 15
<211> LENGTH: 19
<212> TYPE: PRT
<213> ORGANISM: Artificial Sequence
<220> FEATURE:
<223> OTHER INFORMATION: Synthesized

<400> SEQUENCE: 15

Tyr Ser Asp Gly Leu Arg Gln Cys Leu Ala Ala Arg Leu Asp Ala Leu
1               5                   10                  15

Lys Asp Arg

<210> SEQ ID NO 16
<211> LENGTH: 6
<212> TYPE: PRT
<213> ORGANISM: Artificial Sequence
<220> FEATURE:
<223> OTHER INFORMATION: Synthesized

<400> SEQUENCE: 16

His His His His His His
1               5

<210> SEQ ID NO 17
<211> LENGTH: 11
<212> TYPE: PRT
<213> ORGANISM: Artificial Sequence
<220> FEATURE:
<223> OTHER INFORMATION: Synthesized

<400> SEQUENCE: 17

Phe Gln Trp Gln Arg Asn Ile Arg Lys Val Arg
1               5                   10

<210> SEQ ID NO 18
<211> LENGTH: 37
<212> TYPE: PRT
<213> ORGANISM: Artificial Sequence
<220> FEATURE:
<223> OTHER INFORMATION: Synthesized

<400> SEQUENCE: 18

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
                20                  25                  30

Leu Lys Glu Ala Phe
        35

<210> SEQ ID NO 19
<211> LENGTH: 47
<212> TYPE: PRT
<213> ORGANISM: Artificial Sequence
<220> FEATURE:
<223> OTHER INFORMATION: Synthesized

<400> SEQUENCE: 19

Arg Met Arg Ile Thr Glu Arg Asp Phe Arg Gly Gln Met Ser Glu
1               5                   10                  15

Ile Thr Asp Asp Cys Pro Ser Leu Gln Asp Arg Phe His Leu Thr Glu
                20                  25                  30

Val His Ser Leu Arg Val Leu Glu Gly Ser Ser Glu Gln Ile Asp
        35                  40                  45

<210> SEQ ID NO 20
<211> LENGTH: 37
<212> TYPE: PRT
<213> ORGANISM: Artificial Sequence
<220> FEATURE:
<223> OTHER INFORMATION: Synthesized

<400> SEQUENCE: 20

Asp Trp Leu Lys Ala Phe Tyr Asp Lys Val Ala Glu Lys Leu Lys Glu
1               5                   10                  15

Ala Phe Pro Asp Trp Ala Lys Ala Ala Tyr Asp Lys Ala Ala Glu Lys
                20                  25                  30

Ala Lys Glu Ala Ala
        35

<210> SEQ ID NO 21
<211> LENGTH: 37
<212> TYPE: PRT
<213> ORGANISM: Artificial Sequence
<220> FEATURE:
<223> OTHER INFORMATION: Synthesized

<400> SEQUENCE: 21

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
                20                  25                  30

Ala Lys Glu Ala Phe

-continued

35

<210> SEQ ID NO 22
<211> LENGTH: 37
<212> TYPE: PRT
<213> ORGANISM: Artificial Sequence
<220> FEATURE:
<223> OTHER INFORMATION: Synthesized

<400> SEQUENCE: 22

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Ala Lys Glu Ala Ala
        35

<210> SEQ ID NO 23
<211> LENGTH: 36
<212> TYPE: PRT
<213> ORGANISM: Artificial Sequence
<220> FEATURE:
<223> OTHER INFORMATION: Synthesized

<400> SEQUENCE: 23

Trp Leu Lys Ala Phe Tyr Asp Lys Val Ala Glu Lys Leu Lys Glu Ala
1               5                   10                  15

Phe Pro Asp Trp Leu Lys Ala Ala Tyr Asp Lys Val Ala Glu Lys Ala
            20                  25                  30

Lys Glu Ala Ala
        35

<210> SEQ ID NO 24
<211> LENGTH: 37
<212> TYPE: PRT
<213> ORGANISM: Artificial Sequence
<220> FEATURE:
<223> OTHER INFORMATION: Synthesized

<400> SEQUENCE: 24

Asp Trp Leu Lys Ala Phe Tyr Asp Lys Val Ala Glu Lys Leu Lys Glu
1               5                   10                  15

Ala Phe Pro Asp Trp Leu Lys Ala Ala Tyr Asp Lys Ala Ala Glu Lys
            20                  25                  30

Ala Lys Glu Ala Ala
        35

<210> SEQ ID NO 25
<211> LENGTH: 37
<212> TYPE: PRT
<213> ORGANISM: Artificial Sequence
<220> FEATURE:
<223> OTHER INFORMATION: Synthesized

<400> SEQUENCE: 25

Asp Trp Leu Lys Ala Phe Tyr Asp Lys Val Ala Glu Lys Leu Lys Glu
1               5                   10                  15

Ala Phe Pro Asp Trp Gly Lys Ala Gly Tyr Asp Lys Gly Ala Glu Lys
            20                  25                  30

Gly Lys Glu Ala Gly
        35

```
<210> SEQ ID NO 26
<211> LENGTH: 37
<212> TYPE: PRT
<213> ORGANISM: Artificial Sequence
<220> FEATURE:
<223> OTHER INFORMATION: Synthesized

<400> SEQUENCE: 26

Asp Trp Leu Lys Ala Phe Tyr Asp Lys Val Ala Glu Lys Leu Lys Glu
1               5                   10                  15

Ala Phe Pro Asp Trp Gly Lys Ala Gly Tyr Asp Lys Gly Ala Glu Lys
            20                  25                  30

Gly Lys Glu Ala Phe
        35

<210> SEQ ID NO 27
<211> LENGTH: 36
<212> TYPE: PRT
<213> ORGANISM: Artificial Sequence
<220> FEATURE:
<223> OTHER INFORMATION: Synthesized

<400> SEQUENCE: 27

Asp Trp Gly Lys Ala Gly Tyr Asp Lys Gly Ala Glu Lys Gly Lys Glu
1               5                   10                  15

Ala Gly Asp Trp Leu Lys Ala Phe Tyr Asp Lys Val Ala Glu Lys Leu
            20                  25                  30

Lys Glu Ala Phe
        35

<210> SEQ ID NO 28
<211> LENGTH: 34
<212> TYPE: PRT
<213> ORGANISM: Artificial Sequence
<220> FEATURE:
<223> OTHER INFORMATION: Synthesized

<400> SEQUENCE: 28

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys

<210> SEQ ID NO 29
<211> LENGTH: 34
<212> TYPE: PRT
<213> ORGANISM: Artificial Sequence
<220> FEATURE:
<223> OTHER INFORMATION: Synthesized

<400> SEQUENCE: 29

Lys Ala Phe Tyr Asp Lys Val Ala Glu Lys Leu Lys Glu Ala Phe Pro
1               5                   10                  15

Asp Trp Leu Lys Ala Phe Tyr Asp Lys Val Ala Glu Lys Leu Lys Glu
            20                  25                  30

Ala Phe

<210> SEQ ID NO 30
<211> LENGTH: 30
<212> TYPE: PRT
<213> ORGANISM: Artificial Sequence
<220> FEATURE:
```

```
<223> OTHER INFORMATION: Synthesized

<400> SEQUENCE: 30

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Synthesized

<400> SEQUENCE: 31

Asp Lys Val Ala Glu Lys Leu Lys Glu Ala Phe Pro Asp Trp Leu Lys
1               5                   10                  15

Ala Phe Tyr Asp Lys Val Ala Glu Lys Leu Lys Glu Ala Phe
            20                  25                  30

<210> SEQ ID NO 32
<211> LENGTH: 36
<212> TYPE: PRT
<213> ORGANISM: Artificial Sequence
<220> FEATURE:
<223> OTHER INFORMATION: Synthesized

<400> SEQUENCE: 32

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Lys Val Ala Glu Lys Leu
            20                  25                  30

Lys Glu Ala Phe
        35

<210> SEQ ID NO 33
<211> LENGTH: 35
<212> TYPE: PRT
<213> ORGANISM: Artificial Sequence
<220> FEATURE:
<223> OTHER INFORMATION: Synthesized

<400> SEQUENCE: 33

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Val Ala Glu Lys Leu Lys
            20                  25                  30

Glu Ala Phe
        35

<210> SEQ ID NO 34
<211> LENGTH: 36
<212> TYPE: PRT
<213> ORGANISM: Artificial Sequence
<220> FEATURE:
<223> OTHER INFORMATION: Synthesized

<400> SEQUENCE: 34

Asp Trp Leu Ala Phe Tyr Asp Lys Val Ala Glu Lys Leu Lys Glu Ala
1               5                   10                  15

Phe Pro Asp Trp Leu Lys Ala Phe Tyr Asp Lys Val Ala Glu Lys Leu
            20                  25                  30
```

Lys Glu Ala Phe
         35

<210> SEQ ID NO 35
<211> LENGTH: 35
<212> TYPE: PRT
<213> ORGANISM: Artificial Sequence
<220> FEATURE:
<223> OTHER INFORMATION: Synthesized

<400> SEQUENCE: 35

Asp Trp Leu Phe Tyr Asp Lys Val Ala Glu Lys Leu Lys Glu Ala Phe
1               5                   10                  15

Pro Asp Trp Leu Lys Ala Phe Tyr Asp Lys Val Ala Glu Lys Leu Lys
            20                  25                  30

Glu Ala Phe
         35

<210> SEQ ID NO 36
<211> LENGTH: 38
<212> TYPE: PRT
<213> ORGANISM: Artificial Sequence
<220> FEATURE:
<223> OTHER INFORMATION: Synthesized

<400> SEQUENCE: 36

Asp Trp Leu Lys Ala Phe Tyr Asp Lys Val Ala Glu Lys Leu Lys Glu
1               5                   10                  15

Ala Phe Pro Asp Trp Leu Ala Lys Ala Phe Tyr Asp Lys Val Ala Glu
            20                  25                  30

Lys Leu Lys Glu Ala Phe
         35

<210> SEQ ID NO 37
<211> LENGTH: 39
<212> TYPE: PRT
<213> ORGANISM: Artificial Sequence
<220> FEATURE:
<223> OTHER INFORMATION: Synthesized

<400> SEQUENCE: 37

Asp Trp Leu Lys Ala Phe Tyr Asp Lys Val Ala Glu Lys Leu Lys Glu
1               5                   10                  15

Ala Phe Pro Asp Trp Leu Ala Ala Lys Ala Phe Tyr Asp Lys Val Ala
            20                  25                  30

Glu Lys Leu Lys Glu Ala Phe
         35

<210> SEQ ID NO 38
<211> LENGTH: 38
<212> TYPE: PRT
<213> ORGANISM: Artificial Sequence
<220> FEATURE:
<223> OTHER INFORMATION: Synthesized

<400> SEQUENCE: 38

Asp Trp Leu Lys Ala Ala Phe Tyr Asp Lys Val Ala Glu Lys Leu Lys
1               5                   10                  15

Glu Ala Phe Pro Asp Trp Leu Lys Ala Phe Tyr Asp Lys Val Ala Glu
            20                  25                  30

Lys Leu Lys Glu Ala Phe
         35

<210> SEQ ID NO 39
<211> LENGTH: 39
<212> TYPE: PRT
<213> ORGANISM: Artificial Sequence
<220> FEATURE:
<223> OTHER INFORMATION: Synthesized

<400> SEQUENCE: 39

```
Asp Trp Leu Lys Ala Ala Ala Phe Tyr Asp Lys Val Ala Glu Lys Leu
1               5                   10                  15
Lys Glu Ala Phe Pro Asp Trp Leu Ala Phe Tyr Asp Lys Val Ala
            20                  25                  30
Glu Lys Leu Lys Glu Ala Phe
        35
```

<210> SEQ ID NO 40
<211> LENGTH: 37
<212> TYPE: PRT
<213> ORGANISM: Artificial Sequence
<220> FEATURE:
<223> OTHER INFORMATION: Synthesized

<400> SEQUENCE: 40

```
Asp Trp Leu Lys Ala Phe Tyr Asp Lys Val Ala Glu Lys Leu Lys Glu
1               5                   10                  15
Ala Phe Pro Asp Trp Leu Glu Ala Phe Tyr Asp Lys Val Ala Lys Lys
            20                  25                  30
Leu Lys Glu Ala Phe
        35
```

<210> SEQ ID NO 41
<211> LENGTH: 37
<212> TYPE: PRT
<213> ORGANISM: Artificial Sequence
<220> FEATURE:
<223> OTHER INFORMATION: Synthesized

<400> SEQUENCE: 41

```
Asp Trp Leu Lys Ala Phe Tyr Asp Lys Val Ala Glu Lys Leu Lys Glu
1               5                   10                  15
Ala Phe Pro Asp Trp Leu Glu Ala Phe Tyr Asp Glu Val Ala Lys Lys
            20                  25                  30
Leu Lys Lys Ala Phe
        35
```

<210> SEQ ID NO 42
<211> LENGTH: 37
<212> TYPE: PRT
<213> ORGANISM: Artificial Sequence
<220> FEATURE:
<223> OTHER INFORMATION: Synthesized

<400> SEQUENCE: 42

```
Asp Trp Leu Glu Ala Phe Tyr Asp Lys Val Ala Lys Lys Leu Lys Glu
1               5                   10                  15
Ala Phe Pro Asp Trp Leu Lys Ala Phe Tyr Asp Lys Val Ala Glu Lys
            20                  25                  30
Leu Lys Glu Ala Phe
        35
```

<210> SEQ ID NO 43

```
<211> LENGTH: 37
<212> TYPE: PRT
<213> ORGANISM: Artificial Sequence
<220> FEATURE:
<223> OTHER INFORMATION: Synthesized

<400> SEQUENCE: 43

Asp Trp Leu Glu Ala Phe Tyr Asp Glu Val Ala Lys Lys Leu Lys Lys
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 44
<211> LENGTH: 37
<212> TYPE: PRT
<213> ORGANISM: Artificial Sequence
<220> FEATURE:
<223> OTHER INFORMATION: Synthesized

<400> SEQUENCE: 44

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 45
<211> LENGTH: 37
<212> TYPE: PRT
<213> ORGANISM: Artificial Sequence
<220> FEATURE:
<223> OTHER INFORMATION: Synthesized

<400> SEQUENCE: 45

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 46
<211> LENGTH: 37
<212> TYPE: PRT
<213> ORGANISM: Artificial Sequence
<220> FEATURE:
<223> OTHER INFORMATION: Synthesized

<400> SEQUENCE: 46

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 47
<211> LENGTH: 37
<212> TYPE: PRT
<213> ORGANISM: Artificial Sequence
```

```
<220> FEATURE:
<223> OTHER INFORMATION: Synthesized

<400> SEQUENCE: 47

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
        35

<210> SEQ ID NO 48
<211> LENGTH: 37
<212> TYPE: PRT
<213> ORGANISM: Artificial Sequence
<220> FEATURE:
<223> OTHER INFORMATION: Synthesized

<400> SEQUENCE: 48

Leu Leu Asp Asn Trp Asp Ser Val Thr Ser Thr Phe Ser Lys Leu Arg
1               5                   10                  15

Glu Gln Pro Asp Trp Ala Lys Ala Ala Tyr Asp Lys Ala Ala Glu Lys
            20                  25                  30

Ala Lys Glu Ala Ala
        35

<210> SEQ ID NO 49
<211> LENGTH: 37
<212> TYPE: PRT
<213> ORGANISM: Artificial Sequence
<220> FEATURE:
<223> OTHER INFORMATION: Synthesized

<400> SEQUENCE: 49

Leu Glu Ser Phe Lys Val Ser Phe Leu Ser Ala Leu Glu Glu Tyr Thr
1               5                   10                  15

Lys Lys Pro Asp Trp Ala Lys Ala Ala Tyr Asp Lys Ala Ala Glu Lys
            20                  25                  30

Ala Lys Glu Ala Ala
        35

<210> SEQ ID NO 50
<211> LENGTH: 37
<212> TYPE: PRT
<213> ORGANISM: Artificial Sequence
<220> FEATURE:
<223> OTHER INFORMATION: Synthesized

<400> SEQUENCE: 50

Asp Trp Ala Lys Ala Ala Tyr Asp Lys Ala Ala Glu Lys Ala Lys Glu
1               5                   10                  15

Ala Ala Pro Leu Leu Asp Asn Trp Asp Ser Val Thr Ser Thr Phe Ser
            20                  25                  30

Lys Leu Arg Glu Gln
        35

<210> SEQ ID NO 51
<211> LENGTH: 37
<212> TYPE: PRT
<213> ORGANISM: Artificial Sequence
<220> FEATURE:
<223> OTHER INFORMATION: Synthesized
```

-continued

```
<400> SEQUENCE: 51

Asp Trp Ala Lys Ala Ala Tyr Asp Lys Ala Ala Glu Lys Ala Lys Glu
1               5                   10                  15

Ala Ala Pro Leu Glu Ser Phe Lys Val Ser Phe Leu Ser Ala Leu Glu
            20                  25                  30

Glu Tyr Thr Lys Lys
        35

<210> SEQ ID NO 52
<211> LENGTH: 37
<212> TYPE: PRT
<213> ORGANISM: Artificial Sequence
<220> FEATURE:
<223> OTHER INFORMATION: Synthesized

<400> SEQUENCE: 52

Asp Trp Leu Lys Ala Phe Tyr Asp Lys Val Ala Glu Lys Leu Lys Glu
1               5                   10                  15

Ala Phe Pro Ser Asp Glu Leu Arg Gln Arg Leu Ala Ala Arg Leu Glu
            20                  25                  30

Ala Leu Lys Glu Asn
        35

<210> SEQ ID NO 53
<211> LENGTH: 37
<212> TYPE: PRT
<213> ORGANISM: Artificial Sequence
<220> FEATURE:
<223> OTHER INFORMATION: Synethsized

<400> SEQUENCE: 53

Asp Trp Leu Lys Ala Phe Tyr Asp Lys Val Ala Glu Lys Leu Lys Glu
1               5                   10                  15

Ala Phe Pro Arg Ala Glu Leu Gln Glu Gly Ala Arg Gln Lys Leu His
            20                  25                  30

Glu Leu Gln Glu Lys
        35

<210> SEQ ID NO 54
<211> LENGTH: 37
<212> TYPE: PRT
<213> ORGANISM: Artificial Sequence
<220> FEATURE:
<223> OTHER INFORMATION: Synthesized

<400> SEQUENCE: 54

Ser Asp Glu Leu Arg Gln Arg Leu Ala Ala Arg Leu Glu Ala Leu Lys
1               5                   10                  15

Glu Asn Pro Asp Trp Leu Lys Ala Phe Tyr Asp Lys Val Ala Glu Lys
            20                  25                  30

Leu Lys Glu Ala Phe
        35

<210> SEQ ID NO 55
<211> LENGTH: 37
<212> TYPE: PRT
<213> ORGANISM: Artificial Sequence
<220> FEATURE:
<223> OTHER INFORMATION: Synthesized

<400> SEQUENCE: 55

Arg Ala Glu Leu Gln Glu Gly Ala Arg Gln Lys Leu His Glu Leu Gln
```

```
1               5                   10                  15
Glu Lys Pro Asp Trp Leu Lys Ala Phe Tyr Asp Lys Val Ala Glu Lys
                    20                  25                  30

Leu Lys Glu Ala Phe
            35

<210> SEQ ID NO 56
<211> LENGTH: 37
<212> TYPE: PRT
<213> ORGANISM: Artificial Sequence
<220> FEATURE:
<223> OTHER INFORMATION: Synthesized

<400> SEQUENCE: 56

Leu Leu Asp Asn Trp Asp Ser Val Thr Ser Thr Phe Ser Lys Leu Arg
1               5                   10                  15

Glu Gln Pro Ser Asp Glu Leu Arg Gln Arg Leu Ala Ala Arg Leu Glu
                    20                  25                  30

Ala Leu Lys Glu Asn
            35

<210> SEQ ID NO 57
<211> LENGTH: 37
<212> TYPE: PRT
<213> ORGANISM: Artificial Sequence
<220> FEATURE:
<223> OTHER INFORMATION: Synthesized

<400> SEQUENCE: 57

Leu Glu Ser Phe Lys Val Ser Phe Leu Ser Ala Leu Glu Glu Tyr Thr
1               5                   10                  15

Lys Lys Pro Arg Ala Glu Leu Gln Glu Gly Ala Arg Gln Lys Leu His
                    20                  25                  30

Glu Leu Gln Glu Lys
            35

<210> SEQ ID NO 58
<211> LENGTH: 37
<212> TYPE: PRT
<213> ORGANISM: Artificial Sequence
<220> FEATURE:
<223> OTHER INFORMATION: Synthesized

<400> SEQUENCE: 58

Ser Asp Glu Leu Arg Gln Arg Leu Ala Ala Arg Leu Glu Ala Leu Lys
1               5                   10                  15

Glu Asn Pro Leu Leu Asp Asn Trp Asp Ser Val Thr Ser Thr Phe Ser
                    20                  25                  30

Lys Leu Arg Glu Gln
            35

<210> SEQ ID NO 59
<211> LENGTH: 37
<212> TYPE: PRT
<213> ORGANISM: Artificial Sequence
<220> FEATURE:
<223> OTHER INFORMATION: Synthesized

<400> SEQUENCE: 59

Leu Leu Asp Asn Trp Asp Ser Val Thr Ser Thr Phe Ser Lys Leu Arg
1               5                   10                  15

Glu Gln Pro Leu Glu Ser Phe Lys Val Ser Phe Leu Ser Ala Leu Glu
                    20                  25                  30
```

```
                20                  25                  30

Glu Tyr Thr Lys Lys
            35

<210> SEQ ID NO 60
<211> LENGTH: 37
<212> TYPE: PRT
<213> ORGANISM: Artificial Sequence
<220> FEATURE:
<223> OTHER INFORMATION: Synthesized

<400> SEQUENCE: 60

Asp Trp Leu Lys Ala Phe Tyr Asp Lys Val Ala Glu Lys Leu Lys Glu
1               5                   10                  15

Ala Phe Pro Asp Trp Leu Arg Ala Phe Tyr Asp Lys Val Ala Glu Lys
            20                  25                  30

Leu Lys Glu Ala Phe
            35

<210> SEQ ID NO 61
<211> LENGTH: 37
<212> TYPE: PRT
<213> ORGANISM: Artificial Sequence
<220> FEATURE:
<223> OTHER INFORMATION: Synthesized

<400> SEQUENCE: 61

Asp Trp Leu Lys Ala Phe Tyr Asp Lys Val Ala Glu Lys Leu Lys Glu
1               5                   10                  15

Ala Phe Pro Asp Trp Leu Arg Ala Phe Tyr Asp Arg Val Ala Glu Lys
            20                  25                  30

Leu Lys Glu Ala Phe
            35

<210> SEQ ID NO 62
<211> LENGTH: 37
<212> TYPE: PRT
<213> ORGANISM: Artificial Sequence
<220> FEATURE:
<223> OTHER INFORMATION: Synthesized

<400> SEQUENCE: 62

Asp Trp Leu Lys Ala Phe Tyr Asp Lys Val Ala Glu Lys Leu Lys Glu
1               5                   10                  15

Ala Phe Pro Asp Trp Leu Arg Ala Phe Tyr Asp Arg Val Ala Glu Lys
            20                  25                  30

Leu Arg Glu Ala Phe
            35

<210> SEQ ID NO 63
<211> LENGTH: 18
<212> TYPE: PRT
<213> ORGANISM: Artificial Sequence
<220> FEATURE:
<223> OTHER INFORMATION: Synthesized

<400> SEQUENCE: 63

Glu Lys Leu Leu Glu Leu Leu Lys Lys Leu Leu Glu Leu Leu Lys Glu
1               5                   10                  15

Leu Leu

<210> SEQ ID NO 64
```

```
<211> LENGTH: 18
<212> TYPE: PRT
<213> ORGANISM: Artificial Sequence
<220> FEATURE:
<223> OTHER INFORMATION: Synthesized

<400> SEQUENCE: 64

Glu Lys Leu Lys Ala Leu Leu Glu Lys Leu Leu Ala Lys Leu Lys Glu
1               5                   10                  15

Leu Leu

<210> SEQ ID NO 65
<211> LENGTH: 18
<212> TYPE: PRT
<213> ORGANISM: Artificial Sequence
<220> FEATURE:
<223> OTHER INFORMATION: Synthesized

<400> SEQUENCE: 65

Glu Lys Leu Lys Glu Leu Leu Glu Lys Leu Leu Glu Lys Leu Lys Glu
1               5                   10                  15

Leu Leu

<210> SEQ ID NO 66
<211> LENGTH: 18
<212> TYPE: PRT
<213> ORGANISM: Artificial Sequence
<220> FEATURE:
<223> OTHER INFORMATION: Synthesized

<400> SEQUENCE: 66

Glu Glu Leu Lys Glu Lys Leu Glu Glu Leu Lys Glu Lys Leu Glu Glu
1               5                   10                  15

Lys Leu
```